(12) United States Patent
Braun et al.

(10) Patent No.: US 9,101,552 B2
(45) Date of Patent: Aug. 11, 2015

(54) SELF-REVERSIBLE REVERSE LATEX, AND USE THEREOF AS A THICKENING AGENT IN A COSMETIC COMPOSITION

(75) Inventors: Olivier Braun, Castres (FR); Paul Mallo, Croissy-sur-Seine (FR)

(73) Assignee: SOCIETE DEXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 13/641,969

(22) PCT Filed: Apr. 11, 2011

(86) PCT No.: PCT/FR2011/050816
§ 371 (c)(1),
(2), (4) Date: Oct. 18, 2012

(87) PCT Pub. No.: WO2011/138533
PCT Pub. Date: Nov. 10, 2011

(65) Prior Publication Data
US 2013/0035401 A1  Feb. 7, 2013

(30) Foreign Application Priority Data

May 6, 2010 (FR) .................................... 10 53534

(51) Int. Cl.
| | |
|---|---|
| A61K 8/33 | (2006.01) |
| A61Q 19/00 | (2006.01) |
| A61K 8/81 | (2006.01) |
| C08F 220/58 | (2006.01) |
| C09D 133/26 | (2006.01) |
| A61Q 1/14 | (2006.01) |
| A61Q 5/00 | (2006.01) |
| A61Q 5/02 | (2006.01) |
| A61Q 17/04 | (2006.01) |
| A61Q 19/04 | (2006.01) |
| A61Q 19/06 | (2006.01) |
| C08F 220/28 | (2006.01) |
| C08F 222/38 | (2006.01) |

(52) U.S. Cl.
CPC ............... *A61K 8/8158* (2013.01); *A61K 8/33* (2013.01); *A61Q 19/00* (2013.01); *C08F 220/58* (2013.01); *C09D 133/26* (2013.01); *A61Q 1/14* (2013.01); *A61Q 5/00* (2013.01); *A61Q 5/02* (2013.01); *A61Q 17/04* (2013.01); *A61Q 19/002* (2013.01); *A61Q 19/004* (2013.01); *A61Q 19/005* (2013.01); *A61Q 19/008* (2013.01); *A61Q 19/04* (2013.01); *A61Q 19/06* (2013.01); *C08F 220/28* (2013.01); *C08F 222/385* (2013.01); *C08F 2220/286* (2013.01)

(58) Field of Classification Search
None
See application file for complete search history.

(56) References Cited

U.S. PATENT DOCUMENTS

| | | |
|---|---|---|
| 5,368,850 A | 11/1994 | Cauwet et al. |
| 5,458,881 A | 10/1995 | Berger et al. |
| 5,470,551 A | 11/1995 | Dubief et al. |
| 5,510,100 A | 4/1996 | Picard et al. |
| 5,549,681 A | 8/1996 | Segumuller et al. |
| 5,670,471 A | 9/1997 | Amalric et al. |
| 5,679,656 A | 10/1997 | Hansenne |
| 5,888,482 A | 3/1999 | Amalric et al. |
| 5,958,431 A | 9/1999 | Brancq et al. |
| 6,024,946 A | 2/2000 | Dubief et al. |
| 6,287,552 B1 | 9/2001 | Tournilhac et al. |
| 6,353,034 B1 | 3/2002 | Amalric et al. |
| 2008/0312343 A1* | 12/2008 | Braun et al. ............ 514/772.3 |
| 2009/0175811 A1 | 7/2009 | Stolz et al. |
| 2012/0157552 A1 | 6/2012 | Braun et al. |

FOREIGN PATENT DOCUMENTS

| | | |
|---|---|---|
| DE | 19 52 35 96 A1 | 1/1997 |
| EP | 0 161 038 A1 | 11/1985 |
| EP | 0 576 188 A1 | 12/1993 |
| EP | 0 603 019 A1 | 6/1994 |
| EP | 0 604 249 A1 | 6/1994 |
| EP | 0 629 396 A1 | 12/1994 |
| EP | 0 684 024 A2 | 11/1995 |
| EP | 0 715 845 A1 | 6/1996 |
| EP | 0 126 528 A2 | 11/1998 |
| EP | 0 987 017 A1 | 3/2000 |
| EP | 1 623 697 A1 | 2/2006 |
| FR | 2 734 496 A1 | 11/1996 |
| FR | 2 879 607 A1 | 6/2006 |
| GB | 1 482 515 A | 8/1977 |
| WO | 92/06778 A1 | 4/1992 |
| WO | 92/21316 A1 | 10/1992 |
| WO | 92/21318 A1 | 12/1992 |

(Continued)

OTHER PUBLICATIONS

International Search Report, dated Aug. 1, 2011, from corresponding PCT application.

*Primary Examiner* — Michael B Pallay
(74) *Attorney, Agent, or Firm* — Young & Thompson

(57) ABSTRACT

A self-reversible reverse latex, and its use as a thickener. The self-reversible reverse latex includes: 50%-70 of a crosslinked polyelectrolyte obtained by the polymerization of a monomer of formula (I), with R1 being 8 to 20 carbon atoms and $1 \leq n \leq 30$ for a neutral monomer, and a monomer having an acid function; 4%-10% of a water-in-oil emulsifier; 1%-10% of an oil-in-water emulsifier including a surface-active composition (C); 15%-45% oil; and 0%-5% water. Composition (C) is 10%-50% composition ($C_{II}$) and 50%-90% composition($C_{III}$). Composition($C_{II}$) is 60%-100% of a composition of formula (II), with R2 being a 12 carbon alkyl, $T_1$, $T_2$, and $T_3$ being H or a $(-CH_2-CH_2-O-)_{mi}-H$ radical with $0 \leq mi \leq 10$ and $0 < \Sigma mi \leq 10$. Composition ($C_{III}$) is 60%-100% of a compound of formula (III) or mixtures of (III) and (IV), with R2 being as defined previously.

16 Claims, No Drawings

(56) References Cited

FOREIGN PATENT DOCUMENTS

| WO | 93/05762 | A1 | 4/1993 |
| WO | 93/07856 | A1 | 4/1993 |
| WO | 93/08204 | A1 | 4/1993 |
| WO | 93/21316 | A1 | 10/1993 |
| WO | 94/27561 | A1 | 12/1994 |
| WO | 95/04592 | A1 | 2/1995 |
| WO | 95/13863 | A1 | 5/1995 |
| WO | 96/37285 | A1 | 11/1996 |
| WO | 98/09611 | A1 | 3/1998 |
| WO | 98/22207 | A1 | 5/1998 |
| WO | 98/47610 | A1 | 10/1998 |
| WO | 03 061768 | A2 | 7/2003 |

\* cited by examiner

SELF-REVERSIBLE REVERSE LATEX, AND USE THEREOF AS A THICKENING AGENT IN A COSMETIC COMPOSITION

FIELD OF THE INVENTION

The present patent application relates to self-invertible water-in-oil inverse latexes, to their process of preparation and to their application as thickener and/or emulsifier for care products for the skin, scalp or hair or in the manufacture of cosmetic, dermopharmaceutical or pharmaceutical preparations.

BACKGROUND OF THE INVENTION

Inverse latexes based on polyelectrolytes, including partially or completely salified 2-methyl-2-[(1-oxo-2-propenyl) amino]-1-propanesulfonic acid (also known as 2-acrylamido-2-methylpropanesulfonic acid, ATBS or AMPS), and their use in cosmetics and/or pharmaceuticals have formed the subject of numerous patent applications. However, the presence of large amounts of water and oil in these inverse latexes represents a not insignificant disadvantage in terms of volume, cost and sometimes increased risks and/or toxic effects.

Solutions have thus been developed for increasing the concentration of polyelectrolytes in the final inverse latexes, for example by subjecting the reaction medium, at the end of polymerization, to a vacuum distillation stage in order to remove a more or less large portion of water and oil. However, this distillation is problematic to carry out as it often brings about destabilization of the inverse latex, which has to be controlled by the prior addition of stabilizing agents.

European patent applications EP 0 161 038 and EP 0 126 528, and also British patent application GB 1 482 515, disclose such a use of stabilizing polymers. The disadvantage of these stabilizing polymers is that they comprise alcohols or glycols, which can cause environmental problems. Furthermore, the reaction medium sometimes sets solid during the distillation stage, without this phenomenon ever having been truly explained, but the certain consequence of which is the destruction of the batch of inverse latex in the course of manufacture and tiresome and expensive cleaning of the reactor used. Finally, even when the distillation takes place correctly, the inverse latexes obtained are often inverted with difficulty during the processing thereof in an aqueous phase. They also exhibit a high viscosity and sometimes exhibit microgels within them. These disadvantages thus prevent them from being used in the manufacture of cosmetic formulations. In order to overcome these disadvantages, the inventors have developed an inverse latex disclosed in the French patent application published under the number FR 2 879 607, comprising 50% to 80% by weight of a poly-electrolyte comprising from 0.01 mol % to 10 mol % of at least one monomer unit derived from the compound of formula (A):

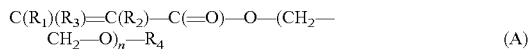

in which the $R_1$, $R_2$ and $R_3$ radicals, which are identical or different, represent, independently of one another, a hydrogen atom or a linear or branched alkyl radical comprising from 1 to 4 carbon atoms, the $R_4$ radical represents a saturated or unsaturated and linear or branched aliphatic radical comprising from 6 to 30 carbon atoms and n represents a number between 1 and 50.

However, when this inverse latex is used to prepare a thickened formulation, its rate of inversion in the aqueous phase, that is to say the time necessary to obtain the maximum development of the viscosity, remains fairly low, which means, for the user, a loss in time which is harmful in the industrial phase. This is because it is well known that the inversion time of inverse latexes increases considerably as a function of the scale of use. Furthermore, the stability over time of the inverse latexes described in FR 2 879 607 is not completely satisfactory. This is because a phenomenon of syneresis is observed with fairly rapid appearance, during storage, of oil at the surface and of a polymer-based residue.

SUMMARY OF THE INVENTION

The inventors have thus sought to develop inverse latexes which do not exhibit the abovementioned dis-advantages.

According to a first aspect, a subject matter of the invention is a composition in the form of a self-invertible inverse latex comprising, for 100% of its weight:
a)—From 50% by weight to 70% by weight of a crosslinked anionic polyelectrolyte (P) obtained by polymerization:
of at least one neutral monomer of formula (I):

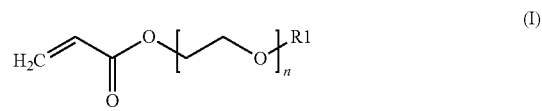

in which the R1 radical represents a linear or branched aliphatic radical comprising from 8 to 20 carbon atoms and n represents a number greater than or equal to one and less than or equal to thirty;
of at least one neutral monomer chosen from acrylamide, N,N-dimethylacrylamide, N-[2-hydroxy-1,1-bis(hydroxymethyl)ethyl]propenamide [or tris(hydroxyl -methyl)acrylamidomethane or N-[tris(hydroxymethyl) -methyl]acrylamide, also known as THAM] or 2-hydroxy -ethyl acrylate; and
of at least one monomer comprising a strong acid functional group and/or of at least one monomer comprising a weak acid functional group;
b)—from 4% by weight to 10% by weight of an emulsifying system ($S_1$) of water-in-oil (W/O) type;
c)—from 1% by weight to 10% by weight of an emulsifying system ($S_2$) of oil-in-water (O/W) type comprising a non zero proportion by weight of a surfactant composition (C), said surfactant composition (C) comprising, for 100 mol %:
1)—a proportion of greater than or equal to 10 mol % and of less than or equal to 50 mol % of a composition ($C_{II}$) comprising, per 100 mol %:
α)—from 60 mol % to 100 mol % of a compound of formula (II):

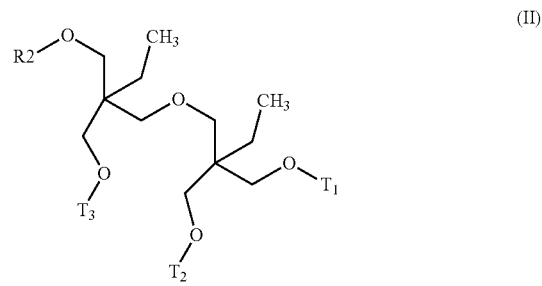

in which:
- R2 represents a linear or branched alkyl radical comprising 12 carbon atoms,
- $T_1$ represents a hydrogen atom or a $(-CH_2-CH_2-O-)_{m1}-H$ radical in which m1 is an integer of greater than or equal to zero and of less than or equal to ten,
- $T_2$, which is identical to or different from $T_1$, represents a hydrogen atom or a $(-CH_2-CH_2-O-)_{m2}-H$ radical in which m2 is an integer of greater than or equal to zero and of less than or equal to ten, and
- $T_3$, which is identical to or different from $T_1$ and $T_2$, represents a hydrogen atom or a $(-CH_2-CH_2-O-)_{m3}-H$ radical in which m3 is an integer of greater than or equal to zero and of less than or equal to ten,
- it being understood that the sum m1+m2+m3 is greater than 0 and less than or equal to ten;
- β)—optionally up to 40 mol % of a compound of formula (II'):

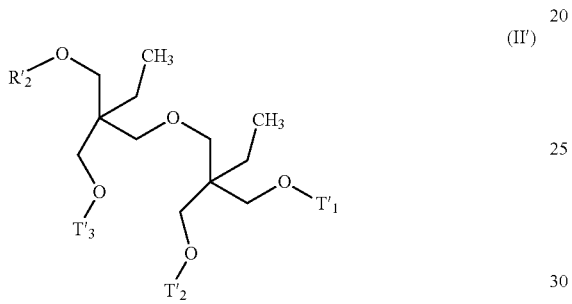

in which:
- R'$_2$ represents a linear or branched alkyl radical comprising 14 carbon atoms,
- T'$_1$ represents a hydrogen atom or a $(-CH_2-CH_2-O-)_{m1}-H$ radical in which m1 is an integer of greater than or equal to zero and of less than or equal to ten,
- T'$_2$, which is identical to or different from T'$_1$, represents a hydrogen atom or a $(-CH_2-CH_2-O-)_{m2}-H$ radical in which m2 is an integer of greater than or equal to zero and of less than or equal to ten, and
- T'$_3$, which is identical to or different from T'$_1$ and T'$_2$, represents a hydrogen atom or a $(-CH_2-CH_2-O-)_{m3}-H$ radical in which m3 is an integer of greater than or equal to zero and of less than or equal to ten,
- it being understood that the sum m1+m2+m3 is greater than 0 and less than or equal to ten; and
- γ)—optionally up to 10 mol % of a compound of formula (II"):

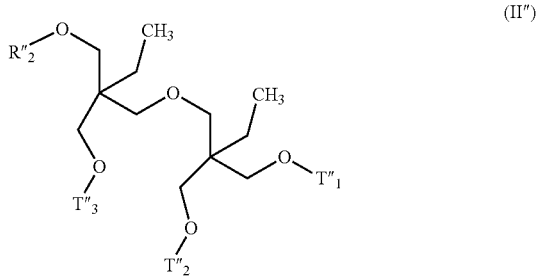

in which:
- R"$_2$ represents a linear or branched alkyl radical comprising 16 carbon atoms,
- T"$_1$ represents a hydrogen atom or a $(-CH_2-CH_2-O-)_{m1}-H$ radical in which m1 is an integer of greater than or equal to zero and of less than or equal to ten,
- T"$_2$, which is identical to or different from T"$_1$, represents a hydrogen atom or a $(-CH_2-CH_2-O-)_{m2}-H$ radical in which m2 is an integer of greater than or equal to zero and of less than or equal to ten, and
- T"$_3$, which is identical to or different from T"$_1$ and T"$_2$, represents a hydrogen atom or a $(-CH_2-CH_2-O-)_{m3}-H$ radical in which m3 is an integer of greater than or equal to zero and of less than or equal to ten,
- it being understood that the sum m1+m2+m3 is greater than 0 and less than or equal to ten;

2)—a proportion of greater than or equal to 50 mol % and of less than or equal to 90 mol % of a composition ($C_{III}$) comprising, per 100 mol %:
- α)—from 60 mol % to 100 mol % of a compound of formula (III):

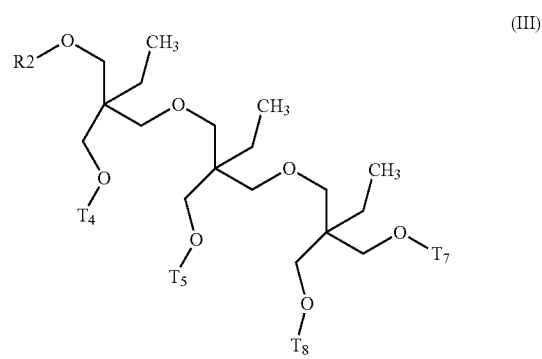

or of its isomer of formula (IV):

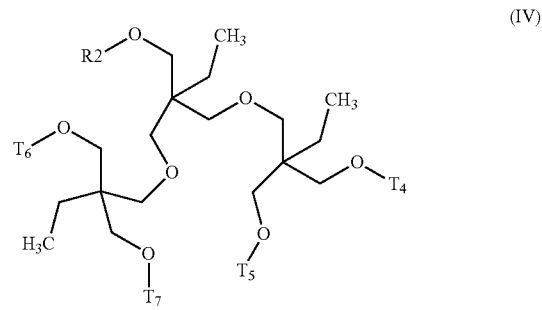

or of the mixture of these two isomers,
in which formulae (III) and (IV):
- R2 represents a linear or branched alkyl radical comprising 12 carbon atoms,
- $T_4$ represents a hydrogen atom or a $(-CH_2-CH_2-O-)_{m4}-H$ radical in which m4 is an integer of greater than or equal to zero and of less than or equal to ten,
- $T_5$, which is identical to or different from $T_4$, represents a hydrogen atom or a $(-CH_2-CH_2-O-)_{m5}-H$ radical in which m5 is an integer of greater than or equal to zero and of less than or equal to ten,
- $T_6$, which is identical to or different from $T_4$ and $T_5$, represents a hydrogen atom or a $(-CH_2-CH_2-O-)_{m6}-H$ radical in which m6 is an integer of greater than or equal to zero and of less than or equal to ten, $T_7$, which is identical to or different from $T_4$, $T_5$ and $T_6$, represents a hydrogen atom or a $(-CH_2-CH_2-O-)_{m7}-H$ radical in which m7 is an integer of greater than or equal to zero and of less than or equal to ten, it being understood that the sum m4+m5+m6+m7 is greater than 0 and less than or equal to ten;

β)—optionally up to 40 mol % of a compound of formula (III'):

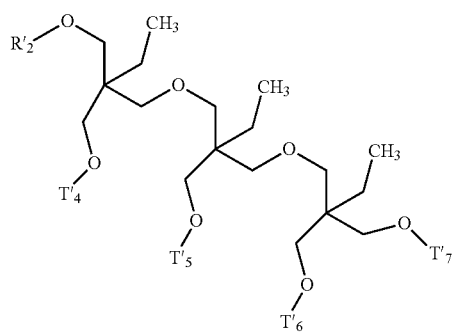

or of its isomer of formula (IV'):

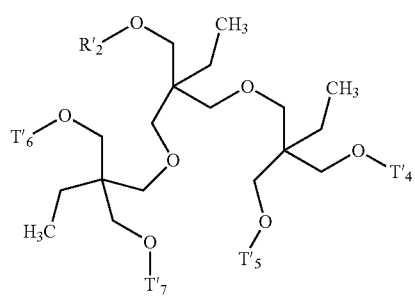

or of the mixture of these two isomers, in which formulae (III') and (IV'):

$R'_2$ represents a linear or branched alkyl radical comprising 14 carbon atoms, $T'_4$ represents a hydrogen atom or a $(-CH_2-CH_2-O-)_{m4}-H$ radical in which m4 is an integer of greater than or equal to zero and of less than or equal to ten, $T'_5$, which is identical to or different from $T'_4$, represents a hydrogen atom or a $(-CH_2-CH_2-O-)_{m5}-H$ radical in which m5 is an integer of greater than or equal to zero and of less than or equal to ten, $T'_6$, which is identical to or different from $T'_4$ and $T'_5$, represents a hydrogen atom or a $(-CH_2-CH_2-O-)_{m6}-H$ radical in which m6 is an integer of greater than or equal to zero and of less than or equal to ten, and $T'_7$, which is identical to or different from $T'_4$, $T'_5$ and $T'_6$, represents a hydrogen atom or a $(-CH_2-CH_2-O-)_{m7}-H$ radical in which m7 is an integer of greater than or equal to zero and of less than or equal to ten, it being understood that the sum m4+m5+m6+m7 is greater than 0 and less than or equal to ten; and γ)—optionally up to 10 mol % of a compound of formula (III''):

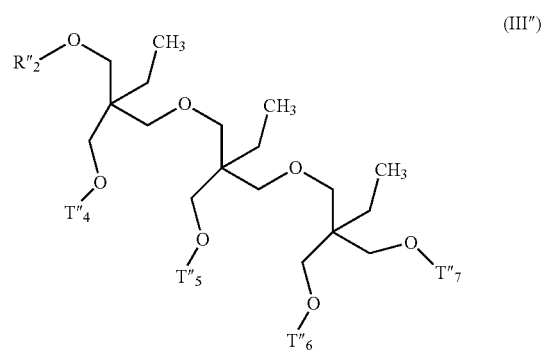

or of its isomer of formula (IV''):

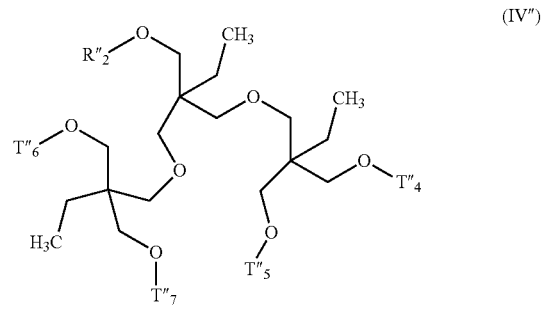

or of the mixture of these two isomers, in which formulae (III'') and (IV''):

$R''_2$ represents a linear or branched alkyl radical comprising 16 carbon atoms, $T''_4$ represents a hydrogen atom or a $(-CH_2-CH_2-O-)_{m4}-H$ radical in which m4 is an integer of greater than or equal to zero and of less than or equal to ten, $T''_5$, which is identical to or different from $T''_4$, represents a hydrogen atom or a $(-CH_2-CH_2-O-)_{m5}-H$ radical in which m5 is an integer of greater than or equal to zero and of less than or equal to ten, $T''_6$, which is identical to or different from $T''_4$ and $T''_5$, represents a hydrogen atom or a $(-CH_2-CH_2-O-)_{m6}-H$ radical in which m6 is an integer of greater than or equal to zero and of less than or equal to ten, and $T''_7$, which is identical to or different from $T''_4$, $T''_5$ and $T''_6$, represents a hydrogen atom or a $(-CH_2-CH_2-O-)_{m7}-H$ radical in which m7 is an integer of greater than or equal to zero and of less than or equal to ten, it being understood that the sum m4+m5+m6+m7 is greater than 0 and less than or equal to ten;

d)—from 15% by weight to 45% by weight of at least one oil, and e)—from 0% by weight to 5% by weight of water.

The term "saturated or unsaturated and linear or branched aliphatic radical comprising from 6 to 20 carbon atoms" denotes, for the R1 radical in the formula (I) as defined above, more particularly linear radicals, such as, for example, the hexyl, octyl, nonyl, decyl, undecyl, dodecyl, tetradecyl, hexadecyl, octadecyl or eicosyl radicals.

DETAILED DESCRIPTION OF THE INVENTION

According to a first specific aspect, in the formula (I) as defined above, the R1 radical represents a lauryl radical or a stearyl radical.

According to another specific aspect, in the formula (I) as defined above, n is greater than or equal to two and less than or equal to twenty.

According to another specific aspect, in the polyelectrolyte P of the composition which is a subject matter of the present invention, the strong acid functional group of the monomers comprising it is in particular the sulfonic acid functional group. Said monomers are, for example, partially or completely salified styrenesulfonic acid or partially or completely salified 2-methyl-2-[(1-oxo-2-propenyl)amino]-1-propanesulfonic acid (also known as 2-acrylamido-2-methylpropanesulfonic acid).

According to another specific aspect, in the polyelectrolyte P included in the composition which is a subject matter of the present invention, the weak acid functional group of the monomers comprising it is in particular the partially salified carboxylic acid functional group. Said monomers are, for example, partially or completely salified acrylic acid, methacrylic acid, itaconic acid, maleic acid or 3-methyl-3-[(1-oxo-2-propenyl)amino]butanoic acid. They are more particularly partially salified acrylic acid or methacrylic acid.

For the monomers comprising a strong acid functional group or comprising a weak acid functional group, the term "salified" indicates that they are alkali metal salts, such as sodium or potassium salts, salts of nitrogenous bases, such as, or the ammonium salt.

A subject matter of the invention is more particularly a composition as defined above for which, in the polyelectrolyte (P), the monomer units comprising a strong acid functional group result from 2-methyl-2-[(1-oxo-2-propenyl)amino]-1-propanesulfonic acid partially or completely salified as sodium salt, as potassium salt or as ammonium salt and the monomer units comprising a weak acid functional group result from acrylic acid or from methacrylic acid partially salified as sodium salt, as potassium salt or as ammonium salt.

A subject matter of the invention is also more particularly a composition as defined above for which the polyelectrolyte (P) comprises, as molar percentage, from 0.5% to 10% of a monomer unit resulting from the monomer of formula (I) as defined above.

According to another specific aspect of the present invention, said surfactant composition (C) as defined above additionally comprises:
3)—up to 5 mol % of a composition ($C_V$) comprising, per 100 mol %:
α)—from 60 mol % to 100 mol % of a compound of formula (V):

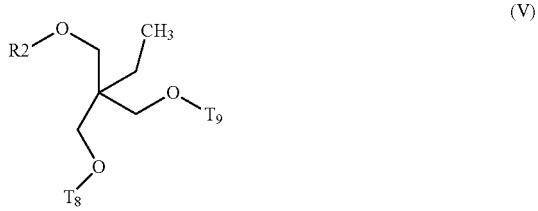

in which:
R2 represents a linear or branched alkyl radical comprising 12 carbon atoms,
$T_8$ represents a hydrogen atom or a (—$CH_2$—$CH_2$—O—)$_{m8}$—H radical in which m8 is an integer of greater than or equal to zero and of less than or equal to ten,
$T_9$, which is identical to or different from $T_8$, represents a hydrogen atom or a (—$CH_2$—$CH_2$—O—)$_{m9}$—H radical in which m9 is an integer of greater than or equal to zero and of less than or equal to ten, and
it being understood that the sum m8+m9 is greater than 0 and less than or equal to ten;
β)—optionally up to 40 mol % of a compound of formula (V'):

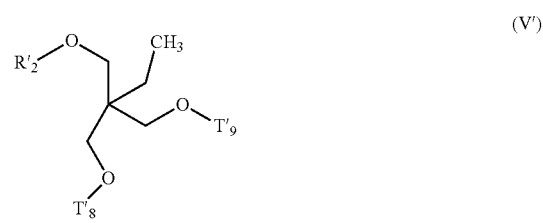

in which:
R'$_2$ represents a linear or branched alkyl radical comprising 14 carbon atoms,
T'$_8$ represents a hydrogen atom or a (—$CH_2$—$CH_2$—O—)$_{m8}$—H radical in which m8 is an integer of greater than or equal to zero and of less than or equal to ten,
T'$_9$, which is identical to or different from T'$_8$, represents a hydrogen atom or a (—$CH_2$—$CH_2$—O—)$_{m9}$—H radical in which m9 is an integer of greater than or equal to zero and of less than or equal to ten, and
it being understood that the sum m8+m9 is greater than 0 and less than or equal to ten; and
γ)—optionally up to 10 mol % of a compound of formula (V"):

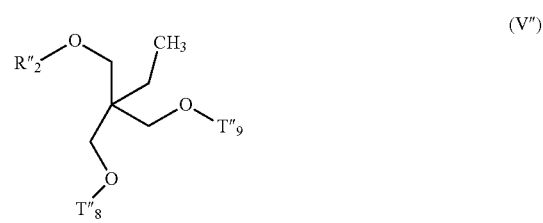

in which:
R"$_2$ represents a linear or branched alkyl radical comprising 16 carbon atoms,
T"$_8$ represents a hydrogen atom or a (—$CH_2$—$CH_2$—O—)$_{m8}$—H radical in which m8 is an integer of greater than or equal to zero and of less than or equal to ten,
T"$_9$, which is identical to or different from T"$_8$, represents a hydrogen atom or a (—$CH_2$—$CH_2$—O—)$_{m9}$—H radical in which m9 is an integer of greater than or equal to zero and of less than or equal to ten, and
it being understood that the sum m8+m9 is greater than 0 and less than or equal to ten.

According to another specific aspect of the present invention, said surfactant composition (C) as defined above additionally comprises:
4)—up to 5 mol % of a composition ($C_{VI}$) comprising, per 100 mol %:
α)—from 60 mol % to 100 mol % of a compound of formula (VI):

R2—(—$CH_2$—$CH_2$—O—)$_{m10}$—H  (VI)

in which R2 represents a linear or branched alkyl radical comprising 12 carbon atoms and m10 is an integer of greater than or equal to zero and of less. than or equal to ten;

β)—optionally up to 40 mol % of a compound of formula (VI'):

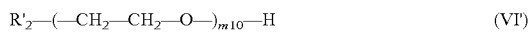

R'$_2$—(—CH$_2$—CH$_2$—O—)$_{m10}$—H    (VI')

in which R'$_2$ represents a linear or branched alkyl radical comprising 14 carbon atoms and m10 is an integer of greater than or equal to zero and of less than or equal to ten; and γ)—optionally up to 10 mol % of a compound of formula (VI''):

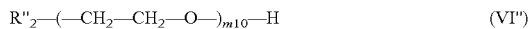

R''$_2$—(—CH$_2$—CH$_2$—O—)$_{m10}$—H    (VI'')

in which R''$_2$ represents a linear or branched alkyl radical comprising 16 carbon atoms and m10 is an integer of greater than or equal to zero and of less than or equal to ten.

According to a specific aspect of the present invention, said surfactant composition (C) as defined above comprises:
1)—a proportion of greater than or equal to 20 mol % and of less than or equal to 50 mol % of a composition (C$_{II}$) as defined above;
2)—a proportion of greater than or equal to 50 mol % and of less than or equal to 80 mol % of a composition (C$_{III}$) as defined above.

According to another specific aspect of the present invention:
1)—said composition (C$_{II}$) comprises, per 100 mol %:
α)—from 60 mol % to 80 mol % of the compound of formula (II),
β)—from 15 mol % to 30 mol % of the compound of formula (II'), and
γ)—up to 10 mol % of the compound of formula (II''), and
2)—said composition (C$_{III}$) comprises, per 100 mol %:
α)—from 60 mol % to 80 mol % of the compound of formula (III), of its isomer of formula (IV) or of the mixture of these isomers,
β)—from 15 mol % to 30 mol % of the compound of formula (III'), of its isomer of formula (IV') or of the mixture of these isomers, and
γ)—up to 10 mol % of the compound of formula (III''), of its isomer of formula (IV'') or of the mixture of these isomers.

In the composition as defined above, the emulsifying system (S$_1$) of water-in-oil (W/O) type is composed either of just one surfactant or of a mixture of surfactants, provided that said surfactant or said mixture has an HLB value which is sufficiently low to bring about water-in-oil emulsions. There is, as emulsifying agent of water-in-oil type, for example, sorbitan esters, such as sorbitan oleate, such as that sold by Seppic under the name Montane™ 80, sorbitan isostearate, such as that sold by Seppic under the name Montane™ 70, or sorbitan sesquioleate, such as that sold by Seppic under the name Montane™ 83. There are also some polyethoxylated sorbitan esters, for example pentaethoxylated sorbitan monooleate, such as that sold by Seppic under the name Montanox™ 81, or penta-ethoxylated sorbitan isostearate, such as that sold under the name Montanox™ 71 by Seppic. There is also diethoxylated oleocetyl alcohol, such as that sold under the name Simulsol™ OC. 72 by Seppic, polyesters with a molecular weight of between 1000 and 3000, products of the condensation between a polyisobutenylsuccinic acid or its anhydride, such as Hypermer™ 2296, sold by Uniqema, or, finally, block copolymers with a molecular weight of between 2500 and 3500, such as Hypermer™ B246, sold by Uniqema, or Simaline™ IE 200, sold by Seppic.

In the composition which is a subject matter of the present invention, the emulsifying system (S$_2$) of oil-in-water (O/W) type comprises at least a non zero amount of the surfactant composition (C) as defined above. The term "non zero amount" denotes more particularly a proportion of greater than or equal to 10% by weight and very particularly of greater than or equal to 50% by weight.

According to a specific form of the present invention, said emulsifying system (S$_2$) of oil-in-water (O/W) type consists of 100% by weight of the surfactant composition (C) as defined above.

According to another specific form of the present invention, the emulsifying system (S$_2$) of oil-in-water (O/W) type additionally comprises at least one emulsifying surfactant of the (O/W) type other than one or other of the compounds as defined above constituting said surfactant composition (C).

The term "emulsifying agent of the oil-in-water type" denotes emulsifying agents having an HLB value sufficiently high to provide oil-in-water emulsions, such as:

ethoxylated sorbitan esters, such as sorbitan oleate polyethoxylated with 20 mol of ethylene oxide, sold by Seppic under the name of Montanox™ 80, or sorbitatn laurate polyethoxylated with 20 mol of ethylene oxide, sold by Seppic under the name of Montanox™ 20;

castor oil polyethoxylated with 40 mol of ethylene oxide, sold under the name Simulsol™ OL50;

decaethoxylated oleodecyl alcohol, sold by Seppic under the name Simulsol™ OC. 710;

heptaethoxylated lauryl alcohol, sold under the name Simulsol™ P7;

or polyethoxylated sorbitan hexaoleates, sold by Seppic under the name Simaline™ IE 400.

According to a specific form of the composition as defined above, the emulsifying system (S$_2$) of oil-in-water (O/W) type additionally comprises a non zero proportion by weight of at least one emulsifying agent of the oil-in-water type chosen from sorbitan oleate polyethoxylated with 20 mol of ethylene oxide; sorbitan laurate polyethoxylated with 20 mol of ethylene oxide; castor oil polyethoxylated with 40 mol of ethylene oxide; decaethoxylated oleodecyl alcohol; heptaethoxylated lauryl alcohol; or polyethoxylated sorbitan hexaoleates.

According to a very specific form of the present invention, said emulsifying system (S$_2$) of oil-in-water (O/W) type comprises, per 100% of its weight:
from 10% by weight to 40% by weight of hepta-ethoxylated lauryl alcohol and
from 60% by weight to 90% by weight of said surfactant composition (C).

The term "branched polyelectrolyte" denotes, for (P), a nonlinear polyelectrolyte which has pendent chains, so as to obtain, when this polyelectrolyte is dissolved in water, a high state of entanglement, resulting in very high viscosities at low gradient.

The term "crosslinked polyelectrolyte" denotes, for (P), a nonlinear polyelectrolyte which is provided in the state of a three-dimensional network which is insoluble in water but which swells with water and which thus results in a chemical gel being obtained.

The composition according to the invention can comprise crosslinked polyelectrolytes and/or branched poly-electrolytes.

When the polyelectrolyte (P) is crosslinked, it is more particularly crosslinked with a diethylenic or polyethylenic compound in a molar proportion, expressed with respect to the monomers employed, which depends on the chemical nature of the crosslinking agent and is generally less than or equal to 0.40 mol %, mainly less than 0.25 mol %, more particularly less than or equal to 0.05 mol % and very particularly between 0.005 mol % and 0.01 mol %. Preferably, the crosslinking agent and/or the branching agent is chosen from ethylene glycol dimethacrylate, diethylene glycol diacrylate, sodium diallyloxyacetate, ethylene glycol diacrylate, diallyl-urea, triallylamine, trimethylolpropane triacrylate, methylenebisacrylamide or a mixture of these compounds.

A subject matter of the invention is more particularly a composition as defined above for which, in the poly-electrolyte (P), the monomer unit resulting from the monomer of formula (I) is a monomer unit resulting from tetraethoxylated lauryl acrylate.

The polyelectrolyte (P) is then preferably chosen from:
crosslinked copolymers of acrylic acid partially salified in the sodium salt or ammonium salt form, of acrylamide and of tetraethoxylated lauryl acrylate;
crosslinked copolymers of 2-methyl-2-[(1-oxo-2-propenyl)amino]-1-propanesulfonic acid partially salified in the sodium salt or ammonium salt form, of acrylamide and of tetraethoxylated lauryl acrylate;
crosslinked copolymers of 2-methyl-2-[(1-oxo-2-propenyl)amino]-1-propanesulfonic acid partially salified in the sodium salt or ammonium salt form, of 2-hydroxyethyl acrylate and of tetraethoxylated lauryl acrylate;
crosslinked copolymers of acrylamide, of 2-methyl-2-[(1-oxo-2-propenyl)amino]-1-propanesulfonic acid, of acrylic acid partially salified in the sodium salt or ammonium salt form and of tetraethoxylated lauryl acrylate;
copolymers of 2-methyl-2-[(1-oxo-2-propenyl)amino]-1-propanesulfonic acid partially salified in the sodium salt or ammonium salt form, of acrylamide, of vinylpyrrolidone and of tetraethoxylated lauryl acrylate; and
crosslinked copolymers of 2-methyl-2-[(1-oxo-2-propenyl)amino]-1-propanesulfonic acid partially or completely salified in the sodium salt form, of acrylic acid partially salified in the sodium salt or ammonium salt form, of 2-hydroxyethyl acrylate, of tris(hydroxyl-methyl)aminomethylacrylamide and of tetraethoxylated lauryl acrylate.

According to another specific aspect of the present invention, the crosslinked anionic polyelectrolyte (P) comprises, per 100% of monomers employed:
from 20 mol % to 80 mol % of monomer units resulting from a monomer comprising either a strong acid functional group or a weak acid functional group;
from 15 mol % to 75 mol % of monomer units resulting from a neutral monomer other than the compound of formula (I) as defined above;
from 0.5 mol % to 5 mol % of monomer units resulting from a monomer of formula (I) as defined above.

According to another specific aspect of the present invention, the crosslinked anionic polyelectrolyte (P) comprises, per 100% of monomers employed:
from 40 mol % to 80 mol % of monomer units resulting from a monomer comprising a strong acid functional group;
from 15 mol % to 55 mol % of monomer units resulting from a neutral monomer other than the compound of formula (I) as defined above;
from 1 mol % to 5 mol % of monomer units resulting from a monomer of formula (I) as defined above.

In the composition which is a subject matter of the present invention, the oil phase is composed either of a commercial mineral oil comprising saturated hydrocarbons, such as paraffins, isoparaffins or cyclo-paraffins, exhibiting at ambient temperature a density between 0.7 and 0.9 and a boiling point of greater than approximately 250° C., such as, for example, Marcol™ 52 or Marcol™ 82, sold by Exxon Chemical, or of a vegetable oil, such as squalane of vegetable origin, or of a synthetic oil, such as hydrogenated polyisobutene or hydrogenated polydecene, or of a mixture of several of these oils. Marcol™ 52 is a commercial oil corresponding to the definition of liquid petrolatums of the codex francais [French Pharmacopeia]. It is a white mineral oil in accordance with the FDA 21 CFR 172.878 and CFR 178.3620 (a) regulations and it is registered in the USA Pharmacopeia, US XXIII (1995), and in the European Pharmacopoeia (1993). The composition according to the invention can also comprise various additives, such as complexing agents, chain-transfer agents or chain-limiting agents.

According to another aspect of the present invention, a subject matter of the latter is a process for the preparation of the composition as defined above, characterized in that:
a) an aqueous phase (A), comprising the monomers and the optional hydrophilic additives, is emulsified in an organic phase (O), comprising the surfactant system ($S_1$), a mixture composed of oil intended to be present in the final composition and a volatile oil, and the optional hydrophobic additives,
b) the polymerization reaction is initiated by introduction, into the emulsion formed in a), of a free radical initiator, and then the polymerization reaction is allowed to take place, and
c) the reaction medium resulting from stage b) is concentrated by distillation until said volatile oil has been completely removed;
d) said emulsifying system ($S_2$) of oil-in-water (O/W) type is introduced, at a temperature of less than or equal to 70° C., into the concentrated medium resulting from stage c).

Volatile oils appropriate for the implementation of the process as defined above are, for example, light iso-paraffins comprising from 8 to 13 carbon atoms, such as, for example, those sold under the Isopar™ G, Isopar™ L, Isopar™ H or Isopar™ J names.

According to a preferred use of the process as defined above, the polymerization reaction is initiated by an oxidation/reduction couple, such as the cumene hydro-peroxide/metabisulfite couple, at a temperature of less than or equal to 10° C., and is then carried out either quasiadiabatically, up to a temperature greater than or equal to 40° C., more particularly of greater than or equal to 50° C., or by controlling the change in the temperature.

The process for the preparation of said surfactant composition (C) as defined above comprises the following successive stages:
A stage a) of reaction of a mixture of alcohols comprising, per 100 mol %:
from 60 mol % to 100 mol % of a compound of formula (VII):

in which R2 represents a linear or branched alkyl radical comprising 12 carbon atoms;
optionally up to 40 mol % of a compound of formula (VII'):

in which $R'_2$ represents a linear or branched alkyl radical comprising 14 carbon atoms, and
optionally up to 10 mol % of a compound of formula (VII"):

in which $R''_2$ represents a linear or branched alkyl radical comprising 16 carbon atoms;

with an excess of 3-(hydroxymethyl)-3-ethyloxetane of formula (VIII):

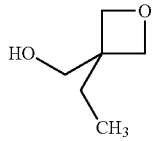
(VIII)

in order to form a composition (C') comprising:

α)—the compound of formula (IX):

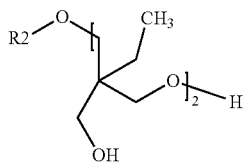
(IX)

in which R2 is as defined above;

β)—optionally the compound of formula (IX'):

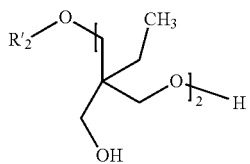
(IX')

in which R'$_2$ is as defined above;

γ)—optionally the compound of formula (IX"):

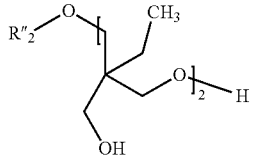
(IX")

in which R"$_2$ is as defined above;

δ)—the compound of formula (X):

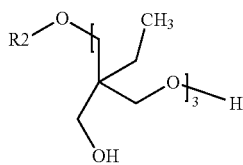
(X)

or its isomer of formula (XI):

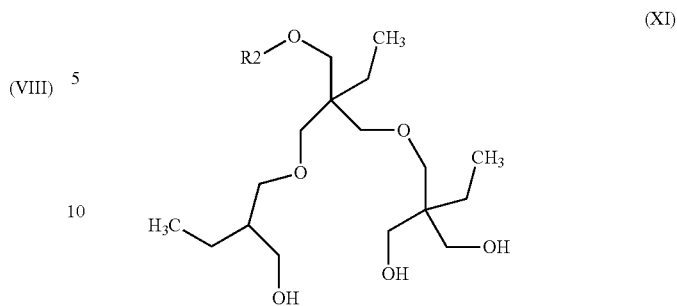
(XI)

or a mixture of these two isomers; in which compounds of formulae (X) and (XI) R2 is as defined above;

ε)—optionally the compound of formula (X'):

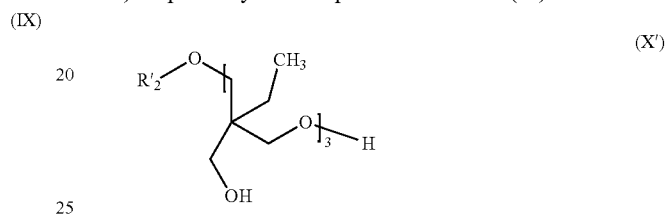
(X')

or its isomer of formula (XI'):

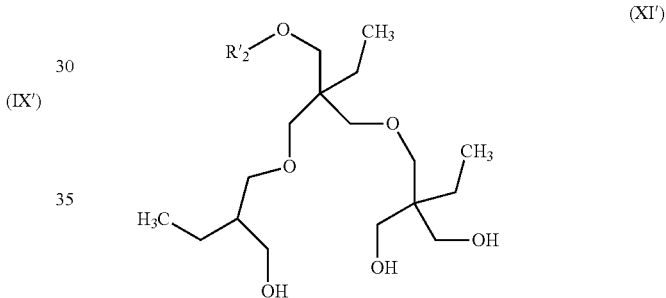
(XI')

or a mixture of these two isomers; in which compounds of formulae (X') and (XI') R'$_2$ is as defined above;

ζ)—optionally the compound of formula (X"):

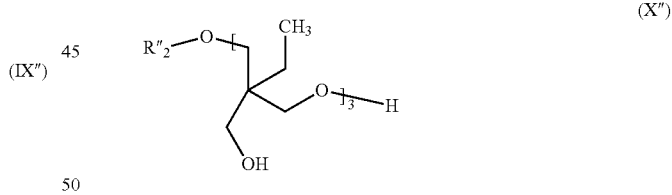
(X")

or its isomer of formula (XI"):

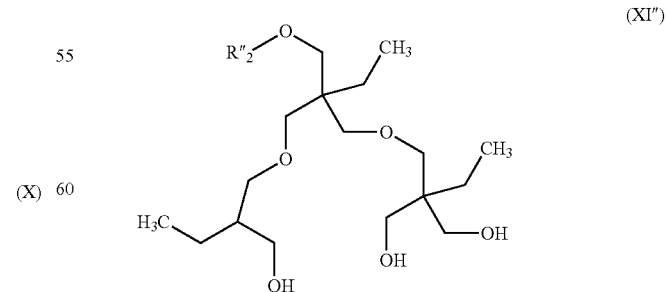
(XI")

or a mixture of these two isomers; in which compounds of formulae (X") and (XI") R"$_2$ is as defined above;

a stage b) of reaction of said composition (C') with ethylene oxide of formula (XII):

 (XII)

in order to form said surfactant composition (C) as defined above.

Another subject matter of the invention is the use of the composition as defined above, as thickening and/or emulsifying agent, to prepare a cosmetic, dermo-pharmaceutical or pharmaceutical topical composition.

Another subject matter of the invention is a cosmetic, dermopharmaceutical or pharmaceutical topical composition, characterized in that it comprises, as thickening and/or emulsifying agent, an effective amount of the composition as defined above.

A topical composition according to the invention, intended to be applied to the skin, scalp or mucous membranes of man or animals, can consist of a topical emulsion comprising at least one aqueous phase and at least one oil phase which is provided in the form of a water-in-oil or oil-in-water or water-in-oil-in-water or oil-in-water-in-oil emulsion. More particularly, this topical emulsion can consist of a fluid emulsion, such as a milk or a fluid gel. The oil phase of the topical emulsion can consist of a mixture of one or more oils.

A topical composition according to the invention can be intended for a cosmetic use or can be used to prepare a medicament intended for the treatment of diseases of the skin, scalp and mucous membranes. In the latter case, the topical composition then comprises an active principle which can, for example, consist of an anti-inflammatory agent, a muscle relaxant, an antifungal or an antibacterial.

When the topical composition is used as cosmetic composition intended to be applied to the skin, to the scalp or to mucous membranes, it may or may not comprise an active principle, for example a moisturizing agent, a tanning agent, a sunscreen, an antiwrinkle agent, an agent having a slimming purpose, an agent for combating free radicals, an antidandruff agent, an antiacne agent or an antifungal.

The term "effective amount" means that the topical composition according to the invention comprises a sufficient amount of inverse latex according to the invention to modify its rheology. The topical composition according to the invention usually comprises between 0.1% and 10% by weight of said self-invertible inverse latex defined above. The pH of the topical composition is generally between 3 and 9.

The topical composition can additionally comprise compounds conventionally included in compositions of this type, for example fragrances, preservatives, colorants, emollients or surfactants.

According to yet another aspect, the invention relates to the use of the abovementioned novel thickening and/or emulsifying agent according to the invention for thickening and emulsifying a topical composition comprising at least one aqueous phase.

The composition according to the invention is an advantageous replacement for those sold under the names Sepigel™ 305, Sepigel™ 501, Simulgel™ EG, Simulgel™ NS or Simulgel™ 600 by the applicant company as it also exhibits good compatibility with other excipients used for the preparation of formulations such as milks, lotions, creams, soaps, baths, balms, shampoos or conditioners. It can also be employed with said Sepigel or Simulgel products. It is compatible in particular with the concentrates described and claimed in the international publications WO 92/06778, WO 95/04592, WO 95/13863, WO 96/37285, WO 98/22207 or WO 98/47610 or in FR 2 734 496, and with the surface-active agents described in WO 93/08204. It is compatible in particular with Montanov™ 68, Montanov™ 82, Montanov™ 202, Montanov™ L, Montanov™ 14 or Montanov™ S. It can also be used in emulsions of the type of those described and claimed in EP 0 629 396 and in cosmetically or physiologically acceptable aqueous dispersions with an organopolysiloxane compound chosen, for example, from those described in WO 93/05762 or in WO 93/21316. It can also be used to form cosmetically or physiologically acceptable aqueous gels having an acid pH, such as those described in WO 93/07856; it can also be used in combination with nonionic celluloses to form, for example, styling gels, such as those described in EP 0 684 024, or also in combination with esters of fatty acids and of sugar to form compositions for treating the hair or the skin, such as those described in EP 0 603 019, or also in shampoos or conditioners, as described and claimed in WO 92/21316, or, finally, in combination with an anionic homopolymer, such as Carbopol™ to form hair treatment products, such as those described in DE 195 23596, or in combination with other thickening polymers.

The composition according to the invention is also compatible with active principles, such as, for example, self-tanning agents, such as dihydroxyacetone (DHA) or antiacne agents; it can thus be introduced into self-tanning compositions, such as those claimed in EP 0 715 845, EP 0 604 249 or EP 0 576 188 or in 93/07902.

It is also compatible with N-acylated derivatives of amino acids, which allows it to be used in soothing compositions, in particular for sensitive skin, such as those described or claimed in WO 92/21318, WO 94/27561 or WO 98/09611, and which also allows it to be used in lightening compositions for the human skin, such as those described or claimed in WO2003/061768.

When the composition as defined above is intended for the treatment of the skin and/or scalp and/or mucous membranes, it more particularly comprises an inverse latex of anionic polyelectrolyte which is a subject matter of the present invention. The inverse latexes which are a subject matter of the present invention can be used as thickener for textile printing pastes.

The aim of the following examples is to illustrate the present invention without, however, limiting it.

EXAMPLE A

Preparation of a Surfactant Composition (C) Employed in the Composition which is a Subject Matter Of the Present Invention Stage A1): Preparation of Intermediate Composition (C')

21 100 g of a mixture of fatty alcohols comprising from 65% to 75% by weight of alkanol comprising 12 carbon atoms, from 21% to 28% by weight of alkanol comprising 14 carbon atoms and from 4% to 8% by weight of alkanol comprising 16 carbon atoms, heated beforehand, are introduced into a reactor and are kept stirred and dried. 326 grams of 50% boron trifluoride in diethyl ether are subsequently added and then 32 600 g of 3-(hydroxymethyl)-3-ethyloxetane are gradually added with stirring over 4 hours while maintaining the temperature at approximately 110° C. The reaction medium is then left at 115° C. for a further 11 hours. The expected composition (C') is then obtained, characterized as follows:

appearance at 25° C.: cloudy gel
acid number (in mg KOH/g; NFT60-204): 3.9
hydroxyl number (in mg KOH/g): 400.5
content by weight of free 3-(hydroxymethyl)-3-ethyloxetane (determined by gas chromatography): <0.05%
content by weight of free alkanols (determined by gas chromatography): $C_{12}$ alkanol: 5.7%; $C_{14}$ alkanol: 2.0%; $C_{16}$ alkanol: 0.5%.

Stage A2): Preparation of the Surfactant Composition (C)

50 000 g of the intermediate composition (C') obtained in the preceding stage A1) are introduced with 75 g of potassium hydroxide into an autoclave with a capacity of 0.1 m³ and are then dried at a temperature of 105° C.

An amount of 35 000 g of ethylene oxide is subsequently gradually introduced while regulating the temperature of the reaction mixture at a value of 125° C. Once the total amount of ethylene oxide has been introduced, the reaction mixture is kept stirred at 125° C. for an additional period of time of one hour. The product then obtained is subsequently cooled to a temperature of 80° C. and emptied out. The surfactant composition (C) is then obtained, characterized as follows:

Appearance at 30° C.: clear liquid
Color: 125 Alpha
Hydroxyl number (in mg KOH/g): 252.5
Acid number (in mg KOH/g) (NFT60-204): 0.08
Residual water content: 0.05%
Cloud point (NF EN 1890E): 76° C.
Content by weight of free alkanols (gas chromatography): $C_{12}$ alkanol: 1.2%; $C_{14}$ alkanol: 0.4%; $C_{16}$ alkanol: 0.1%, i.e. in total 1.7% of residual alkanols.
Viscosity at 25° C. (Brookfield LVT Rotor 3 Speed 12): 1072 mPa·s EXAMPLE 1 (According to the Invention)

Self-Invertible Inverse Latex of the ATBS (Na Salt)/HEA/(LA-4EO) [(ATBS/HEA/(LA-4EO) 89.0/9.9/1.1 Molar] Copolymer Crosslinked with MBA 1) Preparation
   a)—The following are successively introduced with stirring into a first beaker:
   672.5 g of a 55% by weight commercial solution of sodium salt of 2-acrylamido-2-methylpropanesulfonic acid (ATBS Na),
   20.8 g of 2-hydroxyethyl acrylate (HEA);
   0.028 g of methylenebisacrylamide (MBA); and
   1.0 g of a 40% by weight commercial solution of sodium diethylenetriaminepentaacetate.
   The pH therein is then adjusted to 4 by adding, if necessary, the required amount of 2-acrylamido-2-methylpropanesulfonic acid and deionized water up to 700 g.
   b)—The following are successively introduced with stirring into a second beaker:
   130 g of polyisobutene,
   30 g of Marcol™ 52,
   90 g of Isopar™ H,
   17 g of Montane™ 70,
   3 g of Hypermer™ 6212,
   5 g of Simaline™ IE 200,
   7.2 g of tetraethoxylated lauryl acrylate (commercial) (LA-4EO),
   0.36 g of dilauroyl peroxide.
   c)—The aqueous phase is then incorporated in the organic phase with stirring and then the preemulsion thus obtained is subjected to shearing mechanical stirring using a turbine mixer of Silverson type, so as to create a fine emulsion, while sparging with nitrogen.
   d)—After cooling to approximately 8° C., the polymerization reaction is initiated using the oxidation/reduction couple: cumene hydroperoxide/sodium metabisulfite.
   e)—Once the polymerization reaction is complete, the Isopar™ H and virtually all the water are removed by distillation under vacuum.
   f)—After introduction of 2% by weight of Laureth-7 and 4% by weight of the surfactant composition (C) obtained in example A, the self-invertible inverse latex (1) comprising approximately 63% of polymer is obtained, which latex is not very viscous, which very rapidly inverts in water and which has a high thickening power. Moreover, this inverse latex is very stable as no phenomenon of syneresis is observed, in that it releases only a very small amount of oil and in that polymer does not sediment out. Its water content, measured by Karl-Fischer titrimetry, is 1.8% by weight.

2) Viscosity Measurements
   a)—The viscosity of the self-invertible inverse latex (1) obtained as indicated in section 1, that of an aqueous solution devoid of sodium chloride (Sol. 1) and those of aqueous solutions respectively comprising 0.1% by weight (Sol. 2) and 1% by weight (Sol. 3) of sodium chloride, said aqueous solutions each comprising 2% by weight of said self-invertible inverse latex (1), are measured. The results, measured using a Brookfield RVT viscometer, are recorded in the following table:

|  | Rotor (R); Rotational speed of the rotor (S) (in revolutions per minute) | Viscosity (in mPa · s) |
| --- | --- | --- |
| Inverse latex (1) | R 3, S 20 | 2700 |
| Sol. 1 | R 6, S 5 | 54 000 |
| Sol. 2 | R 6, S 5 | 27 000 |
| Sol. 3 | R 3, S 5 | 1600 |

3) Measurement of the Inversion Time and Evaluation of The Stability of the Inverse Latex
   a)—The inversion time is evaluated by measuring the time necessary in order to obtain a smooth and homogeneous gel for a 2% by weight aqueous solution of self-invertible inverse latex (1) under the standard conditions for measuring this viscosity, that is to say by incorporating 16 g of the inverse latex (1) in 784 g of water, the combined mixture being placed in a 1 liter low-form beaker, and then by stirring the combined mixture using a butterfly-type axial-flow impeller rotating at 150 revolutions per minute. The inversion time is thus the duration evaluated between starting the stirrer and the appearance of a smooth and homogeneous medium in the beaker. In the present example, the inversion time is 50 seconds.
   b)—The stability of the inverse latex is evaluated by observing the time for appearance of an oil layer at the surface. In the present example, the time for appearance of the oil layer at the surface of inverse latex (1) is two weeks.

EXAMPLE T1 (ACCORDING TO THE STATE OF THE ART)

Self-Invertible Inverse Latex of the ATBS (Na Salt)/HEA/(LA-4EO) [(ATBS/HEA/(LA-4EO) 89.0/9.9/1.1 Molar] Copolymer Crosslinked with MBA 1) Preparation Stages a) to d) of example 1 are reproduced. In stage f), 4% by weight of Montanox™ 20 are added in place of 4% by weight of the surfactant composition (C) and the self-invertible inverse latex (T1) is obtained.

2) Viscosity measurements
   a)—The viscosity of the self-invertible inverse latex (T1) obtained as indicated in section 1, that of an aqueous solution devoid of sodium chloride (Sol. 4) and those of aqueous solutions respectively comprising 0.1% by weight (Sol. 5) and 1% by weight (Sol. 6) of sodium chloride, said aqueous solutions each comprising 2% by weight of said self-invertible inverse latex (T1), are measured. The results, measured using a Brookfield RVT viscometer, are recorded in the following table:

|  | Rotor (R); Rotational speed of the rotor (S) (in revolutions per minute) | Viscosity (in mPa · s) |
|---|---|---|
| Inverse latex (T1) | R 3, S 20 | 2900 |
| Sol. 4 | R 6, S 5 | 51 200 |
| Sol. 5 | R 6, S 5 | 25 200 |
| Sol. 6 | R 3, S 5 | 1300 |

3) Measurement of the inversion time and evaluation of the stability of the inverse latex
   a)—The inversion time, evaluated in the same way as in the preceding example, is 2 minutes 20 seconds.
   b)—The stability of the inverse latex (T1) is evaluated in the same way as in the preceding example. Significant release of oil is observed after one week.

EXAMPLE 2 (ACCORDING TO THE INVENTION)

Self-Invertible Inverse Latex of the ATBS (Na Salt)/HEA/(LA-4EO) [(ATBS/HEA/(LA-4EO) 89.0/9.9/1.1 Molar] Copolymer Crosslinked with MBA 1) Preparation Stages a) to d) of example 1 are reproduced. In stage f), only 4% by weight of the surfactant composition (C) are added and the self-invertible inverse latex (2) is obtained.

2) Viscometry, measurement of the inversion time and evaluation of the stability of the inverse latex (2)
   a)—The viscometric performance of the inverse latex (2) is similar to that reported for the inverse latex of example 1.
   b)—The inversion time of the inverse latex (2), evaluated in the same way as in example 1, is approximately 40 seconds.
   c)—The stability of the inverse latex (2) is evaluated in the same way as in example 1. The time for appearance of the oil layer is a few days.

EXAMPLE T2 (ACCORDING TO THE STATE OF THE ART)

Self-Invertible Inverse Latex of the ATBS (Na Salt)/HEA/(LA-4EO) [(ATBS/HEA/(LA-4EO) 89.0/9.9/1.1 Molar] Copolymer Crosslinked With MBA 1) Preparation Stages a) to d) of example 1 are reproduced. In stage f), 4% by weight of a composition (C''') are added, which composition comprises, per 100 mol %:
   i)—a proportion of greater than or equal to 10 mol % and of less than or equal to 50 mol % of a compound of formula (II''') corresponding to the formula (II) in which R2 represents a linear or branched alkyl radical comprising 10 carbon atoms and in which the sum m1+m2+m3 is equal to 5;
   ii)—a proportion of greater than or equal to 50 mol % and of less than or equal to 90 mol % of a compound of formula (III''') or of its isomer of formula (IV''') or of the mixture of these two isomers, formulae (III''') and (IV''') respectively corresponding to the formulae (III) and (IV) in which R2 represents a linear or branched alkyl radical comprising 10 carbon atoms and in which the sum m4+m5+m6+m7 is equal to 5; and the self-invertible inverse latex (T2) is obtained.

2) Viscometry, Measurement of the Inversion Time and Evaluation of the Stability of the Inverse Latex (T2)
   a)—The viscometric performance of the inverse latex (T2) is similar to that reported for the inverse latex of example 1.
   b)—The inversion time of the inverse latex (T2), evaluated in the same way as in example 1, is approximately 50 seconds.
   c)—The stability of the inverse latex (T2) is evaluated in the same way as in example 1. The time for appearance of the oil layer is a few hours.

EXAMPLE T3 (ACCORDING TO THE STATE OF THE ART)

Self-Invertible Inverse Latex of the AM/AA/(LA-4EO) [(AM/AA/(LA-4EO) 24.7/74.1/1.2 Molar] Copolymer Crosslinked with MBA 1) Preparation
   a)—The following are successively introduced with stirring into a first beaker:
   106.5 g of a 50% (by weight) commercial acrylamide (AM) solution,
   162.0 g of glacial acrylic acid (AA),
   98.1 g of a 29.3% by weight aqueous ammonium solution,
   0.047 g of methylenebisacrylamide (MBA),
   0.45 g of a 40% commercial solution of sodium diethylenetriaminepentaacetate,
   deionized water up to 680 g.
   b)—The following are successively introduced with stirring into a second beaker:
   121 g of polyisobutene,
   28 g of Marcol™ 52,
   99 g of Isopar™ H,
   17 g of Montane™ 70,
   3 g of Hypermer™ 2296,
   5 g of Simaline™ IE 200, 1.2 g of tetraethoxylated lauryl acrylate (commercial) (LA-4EO),
0.1 g of AIBN.
c)—The aqueous phase is then incorporated in the organic phase with stirring and then the preemulsion thus obtained is subjected to shearing mechanical stirring using a turbine mixer of Silverson type, so as to create a fine emulsion, while sparging with nitrogen.
d)—After cooling to approximately 8° C., the polymerization reaction is initiated using the oxidation/reduction couple: cumene hydroperoxide/sodium metabisulfite.
e)—Once the polymerization reaction is complete, the Isopar™ H and virtually all the water are removed by distillation under vacuum.
f)—After introduction of 4% of Montanox™ 20 and 2% of Laureth-7, the self-invertible inverse latex (T3) is obtained, which latex comprises approximately 63% of polymer, is not very viscous, inverts very rapidly in water and has a high thickening power. Its water content, measured by Karl-Fischer titrimetry, is 1.8% by weight.

2) Viscosity Measurements
a)—The viscosity of the self-invertible inverse latex (T3) obtained as indicated in section 1, that of an aqueous solution devoid of sodium chloride (Sol. 7) and those of aqueous solutions respectively comprising 0.1% by weight (Sol. 8) and 1% by weight (Sol. 9) of sodium chloride, said aqueous solutions each comprising 2% by weight of said self-invertible inverse latex (T3), are measured. The results, measured using a Brookfield RVT viscometer, are recorded in the following table:

|  | Rotor (R); Rotational speed of the rotor (S) (in revolutions per minute) | Viscosity (in mPa · s) |
|---|---|---|
| Inverse latex (T3) |  | nd |
| Sol. 7 | R 6, S 5 | 79 400 |
| Sol. 8 | R 6, S 5 | 45 200 |
| Sol. 9 | R 3, S 5 | 3300 | nd: not determined

3) Measurement of the Inversion Time and Evaluation of the Stability of the Inverse Latex (T3)
b)—The inversion time of the inverse latex (T3), evaluated in the same way as in example 1, is approximately 2 minutes.
c)—The stability of the inverse latex (T3) is evaluated in the same way as in example 1. The time for appearance of the oil layer is two weeks.

EXAMPLE 3 (ACCORDING TO THE INVENTION)

Self-Invertible Inverse Latex of the AM/AA/(LA-4EO) [(AM/AA/(LA-4EO) 24.7/74.1/1.2 Molar] Copolymer Crosslinked with MBA 1) Preparation
Stages a) to d) of example T3 are reproduced. In stage f), 2% by weight of Laureth-7 and 4% by weight of the surfactant composition (C) are added in place of the 4% of Montanox™ 20 and 2% of Laureth-7 of said example T3 and the self-invertible inverse latex (3) is obtained.

2) Viscometry, Measurement of the Inversion Time and Evaluation of the Stability of the Inverse Latex (3)
a)—The viscometric performance of the inverse latex (3) is similar to that reported for the inverse latex of example T3.
b)—The inversion time of the inverse latex (3), evaluated in the same way as in example 1, is approximately 30 seconds.
c)—The stability of the inverse latex (3) is evaluated in the same way as in example 1. The time for appearance of the first drops of oil is three weeks.

EXAMPLE 4 (ACCORDING TO THE INVENTION)

Self-Invertible Inverse Latex of the ATBS (Na Salt)/AA/HEA/THAM/(LA-4EO) [ATBS/AA/HEA/THAM/(LA-4EO) 83.9/1.9/9.3/3.7/1.2 Molar] Copolymer Crosslinked with MBA 1) Preparation
a)—The following are successively introduced with stirring into a first beaker:
672.5 g of a 55% (by weight) commercial solution of the sodium salt of 2-acrylamido-2-methylpropane-sulfonic acid (ATBSNa);
20.8 g of 2-hydroxyethyl acrylate;
12.6 g of THAM;
2.6 g of acrylic acid (AA);
0.041 g of methylenebisacrylamide (MBA);
0.45 g of a 40% commercial solution of sodium diethylenetriaminepentaacetate.
The pH therein is then adjusted to 4 by adding, if necessary, the required amount of 2-acrylamido-2-methylpropane-sulfonic acid and deionized water up to 700 g.
b)—The following are successively introduced with stirring into a second beaker:
130 g of polyisobutene,
30 g of Marcol™ 52,
90 g of Isopar™ H,
17 g of Montane™ 70,
5 g of Hypermer™6212,
3 g of Dehymuls PGPH (polyglyceryl polyhydroxy-stearate),
7.4 g of tetraethoxylated lauryl acrylate (commercial) (LA-4EO),
0.14 g of dilauroyl peroxide.
c)—The aqueous phase is then introduced into the organic phase with stirring and then the preemulsion thus obtained is subjected to shearing mechanical stirring using a turbine mixer of Silverson type, so as to create a fine emulsion, while sparging with nitrogen.
d)—After cooling to approximately 8° C., the polymerization reaction is initiated using the oxidation/reduction couple: cumene hydroperoxide/sodium metabisulfite.
e)—Once the polymerization reaction is complete, the Isopar™ H and virtually all the water are removed by distillation under vacuum.
f)—After introduction of 2% by weight of Laureth-7 and 4% by weight of the surfactant composition (C) obtained in example A, the self-invertible inverse latex (4) is obtained, which latex comprises approximately 63% of polymer, is not very viscous, inverts very rapidly in water and has a high thickening power. Its water content, measured by Karl-Fischer titrimetry, is 2.2% by weight.

2) Viscosity Measurements a)—The viscosity of the self-invertible inverse latex (4) obtained as indicated in section 1, that of an aqueous solution devoid of sodium chloride (Sol. 10) and that of an aqueous solution comprising 0.1% by weight (Sol. 11) of sodium chloride, said aqueous solutions each comprising 2% by weight of said self-invertible inverse latex (4), are measured. The results, measured using a Brookfield RVT viscometer, are recorded in the following table:

|  | Rotor (R); Rotational speed of the rotor (S) (in revolutions per minute) | Viscosity (in mPa · s) |
|---|---|---|
| Inverse latex (4) | R 3, S 20 | 1100 |
| Sol. 10 | R 6, S 5 | 66 200 |
| Sol. 11 | R 6, S 5 | 16 500 |

3) Measurement of the Inversion Time and Evaluation of The Stability of the Inverse Latex b)—The inversion time of the inverse latex (4), evaluated in the same way as in example 1, is approximately 30 seconds.

c)—The stability of the inverse latex (4) is evaluated in the same way as in example 1. The time for appearance of the first drops of oil is three weeks.

EXAMPLES OF COSMETIC FORMULATIONS (PROPORTIONS EXPRESSED AS PERCENTAGES BY WEIGHT)

EXAMPLE 5

Care Cream

| Cyclomethicone: | 10% |
|---|---|
| Self-invertible inverse latex (1): | 0.8% |
| Montanov ™ 68: | 4.5% |
| Preservative: | 0.65% |
| Lysine: | 0.025% |
| EDTA (disodium salt): | 0.05% |
| Xanthan gum: | 0.2% |
| Glycerol: | 3% |
| Water: | q.s. for 100% |

EXAMPLE 6

Care Cream

| Cyclomethicone: | 10% |
|---|---|
| Self-invertible inverse latex (3): | 0.8% |
| Montanov ™ 68: | 4.5% |
| Perfluoro-polymethyl-isopropyl ether: | 0.5% |
| Preservative: | 0.65% |
| Lysine: | 0.025% |
| EDTA (disodium salt): Pemulen ™ TR: | 0.05% |
| Glycerol: | 3% |
| Water: | q.s. for 100% |

EXAMPLE 7

Aftershave Balm

| | FORMULA | |
|---|---|---|
| A | Self-invertible inverse latex (2): | 1.5% |
| | Water: | q.s. for 100% |
| B | Micropearl ™ M100: | 5.0% |
| | Sepicide ™ CI: | 0.50% |
| | Fragrance: | 0.20% |
| | 95° of ethanol: | 10.0% |

PROCEDURE

B is added to A.

EXAMPLE 8

Satin Emulsion for the Body

| | FORMULA | |
|---|---|---|
| A | Simulsol ™ 165: | 5.0% |
| | Lanol ™ 1688: | 8.50% |
| | Shea butter: | 2% |
| | Liquid paraffin: | 6.5% |
| | Lanol ™ 14 M: | 3% |
| | Lanol ™ S: | 0.6% |
| B | Water: | 66.2% |
| C | Micropearl ™ M 100: | 5% |
| D | Self-invertible inverse latex (4): | 3% |
| E | Sepicide ™ CI | 0.3% |
| | Sepicide ™ HB: | 0.5% |
| | Monteine ™ CA: | 1% |
| | Fragrance: | 0.20% |
| | Vitamin E acetate: | 0.20% |
| | Sodium pyrrolidinonecarboxylate (moisturizing agent): | 1% |

PROCEDURE

C is added to B, B is emulsified in A at 70° C., D is then added at 60° C. and then E is added at 30° C.

EXAMPLE 9

Body Milk

| | FORMULA | |
|---|---|---|
| A | Simulsol ™ 165: | 5.0% |
| | Lanol ™ 1688: | 12.0% |
| | Lanol ™ 14 M: | 2.0% |
| | Cetyl alcohol: | 0.3% |
| | Schercemol ™ OP: | 3% |
| B | Water: | q.s. for 100% |
| C | Self-invertible inverse latex (3): | 0.35% |
| D | Sepicide ™ CI: | 0.2% |
| | Sepicide ™ HB: | 0.5% |
| | Fragrance: | 0.20% |

PROCEDURE

B is emulsified in A at 70° C., C is added, then D is added at 60° C. and then E is added at 30° C.

EXAMPLE 10

O/W Cream

FORMULA

| | | |
|---|---|---|
| A | Simulsol ™ 165: | 5.0% |
| | Lanol ™ 1688: | 20.0% |
| | Lanol ™ P: | 1.0% |
| B | Water: | q.s. for 100% |
| C | Self-invertible inverse latex (2): | 2.50% |
| D | Sepicide ™ CI: | 0.20% |
| | Sepicide ™ HB: | 0.30% |

PROCEDURE
B is introduced into A at approximately 75° C., C is added at approximately 60° C. and then D is added at approximately 45° C.

EXAMPLE 11

Nonfatty Antisun Gel

FORMULA

| | | |
|---|---|---|
| A | Self-invertible inverse latex (1): | 3.00% |
| | Water: | 30% |
| B | Sepicide ™ C | 0.20% |
| | Sepicide ™ HB: | 0.30% |
| | Fragrance: | 0.10% |
| C | Colorant: | q.s. |
| | Water: | 30% |
| D | Micropearl ™ M 100: | 3.00% |
| | Water: | q.s. for 100% |
| E | Silicone oil: | 2.0% |
| | Parsol ™ MCX: | 5.00% |

PROCEDURE
B is introduced into A, C is added, then D is added and then E is added.

EXAMPLE 12

Antisun Milk

FORMULA

| | | |
|---|---|---|
| A | Sepiperl ™ N: | 3.0% |
| | Sesame oil: | 5.0% |
| | Parsol ™ MCX: | 5.0% |
| | Carrageenan: | 0.10% |
| B | Water: | q.s. for 100% |
| C | Self-invertible inverse latex (3): | 0.80% |
| D | Fragrance: | q.s. |
| | Preservative: | q.s. |

PROCEDURE
B is emulsified in A at 75° C., then C is added at approximately 60° C., then D is added at approximately 30° C. and, if necessary, the pH is adjusted.

EXAMPLE 13

Massage Gel

FORMULA

| | | |
|---|---|---|
| A | Self-invertible inverse latex (2): | 3.5% |
| | Water: | 20.0% |
| B | Colorant: | 2 drops/100 g |
| | Water: | q.s. |
| C | Alcohol: | 10% |
| | Menthol: | 0.10% |
| D | Silicone oil: | 5.0% |

PROCEDURE
B is added to A, then C is added to the mixture, followed by D.

EXAMPLE 14

Massage Care Gel

FORMULA

| | | |
|---|---|---|
| A | Self-invertible inverse latex (3): | 3.00% |
| | Water: | 30% |
| B | Sepicide ™ CI: | 0.20% |
| | Sepicide ™ HB: | 0.30% |
| | Fragrance: | 0.05% |
| C | Colorant: | q.s. |
| | Water: | q.s. for 100% |
| D | Micropearl ™ SQL: | 5.0% |
| | Lanol ™ 1688: | 2% |

PROCEDURE
A is prepared, B is added, then C is added, then D is added.

EXAMPLE 15

Radiance Gel

FORMULA

| | | |
|---|---|---|
| A | Self-invertible inverse latex (4): | 4% |
| | Water: | 30% |
| B | Elastine HPM: | 5.0% |
| C | Micropearl ™ M 100: | 3% |
| | Water: | 5% |
| D | Sepicide ™ CI: | 0.2% |
| | Sepicide ™ HB: | 0.3% |
| | Fragrance: | 0.06% |
| | 50% Sodium pyrrolidinonecarboxylate: | 1% |
| | Water: | q.s. for 100% |

PROCEDURE
A is prepared, B is added, then C is added and then D is added.

EXAMPLE 16

Body Milk

FORMULA

| | | |
|---|---|---|
| A | Sepiperl ™ N: | 3.0% |
| | Glyceryl triheptanoate: | 10.0% |
| B | Water: | q.s. for 100% |
| C | Self-invertible inverse latex (1): | 1.0% |
| D | Fragrance: | q.s. |
| | Preservative: | q.s. |

PROCEDURE
A is melted at approximately 75° C. B is emulsified in A at 75° C., then C is added at approximately 60° C. and then D is added.

EXAMPLE 17

Make-Up-Removing Emulsion Comprising Sweet Almond Oil

| FORMULATION | |
|---|---|
| Montanov ™ 68: | 5% |
| Sweet almond oil: | 5% |
| Water: | q.s. for 100% |
| Self-invertible inverse latex (4): | 0.3% |
| Glycerol: | 5% |
| Preservative: | 0.2% |
| Fragrance: | 0.3% |

EXAMPLE 18

Moisturizing Cream for Greasy Skin

| FORMULA | |
|---|---|
| Montanov ™ 68: | 5% |
| Cetearyl octanoate: | 8% |
| Octyl palmitate: | 2% |
| Water: | q.s. for 100% |
| Self-invertible inverse latex (3): | 0.6% |
| Micropearl ™ M 100: | 3.0% |
| Mucopolysaccharides: | 5% |
| Sepicide ™ HB: | 0.8% |
| Fragrance: | 0.3% |

EXAMPLE 19

Alcohol-Free Soothing Aftershave Balm

| FORMULA | |
|---|---|
| Mixture of N-lauryl amino acids: | 0.1% to 5% |
| Magnesium potassium aspartate | 0.002% to 0.5% |
| Lanol ™ 99: | 2% |
| Sweet almond oil: | 0.5% |
| Water: | q.s. for 100% |
| Self-invertible inverse latex (2): | 3% |
| Sepicide ™ HB: | 0.3% |
| Sepicide ™ CI: | 0.2% |
| Fragrance: | 0.4% |

EXAMPLE 20

Cream Comprising AHAS for Sensitive Skin

| FORMULA | |
|---|---|
| Mixture of N-lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | q.s. for 100% |
| Self-invertible inverse latex (1): | 1.50% |
| Gluconic acid: | 1.50% |
| Triethanolamine: | 0.9% |
| Sepicide ™ NB: | 0.3% |
| Sepicide ™ CI: | 0.2% |
| Fragrance: | 0.4% |

EXAMPLE 21

Soothing after-Sun Care Product

| FORMULA | |
|---|---|
| Mixture of N-lauryl amino acids: | 0.1% to 5% |
| Magnesium potassium aspartate: | 0.002% to 0.5% |
| Lanol ™ 99: | 10.0% |
| Water: | q.s. for 100% |
| Self-invertible inverse latex (4): | 2.50% |
| Sepicide ™ HB: | 0.3% |
| Sepicide ™ CI: | 0.2% |
| Fragrance: | 0.4% |
| Colorant: | 0.03% |

EXAMPLE 22

Make-Up-Removing Milk

| FORMULA | |
|---|---|
| Sepiperl ™ N: | 3% |
| Primol ™ 352: | 8.0% |
| Sweet almond oil: | 2% |
| Water: | q.s. for 100% |
| Self-invertible inverse latex (3): | 0.8% |
| Preservative: | 0.2% |

EXAMPLE 23

Body Milk

| FORMULA | |
|---|---|
| Sepiperl ™ N: | 3.5% |
| Lanol ™ 37T: | 8.0% |
| Solagum ™ L: | 0.05% |
| Water: | q.s. for 100% |
| Benzophenone: | 2.0% |
| Dimethicone 350 cPs: | 0.05% |
| Self-invertible inverse latex (1) | 0.8% |
| Preservative: | 0.2% |
| Fragrance: | 0.4% |

EXAMPLE 24

Fluid Emulsion Having an Alkaline pH

| FORMULA | |
|---|---|
| Marcol ™ 82: | 5.0% |
| NaOH | 10.0% |

-continued

| FORMULA | |
|---|---|
| Water: | q.s. for 100% |
| Self-invertible inverse latex (2): | 1.5% |
| Lanol ™ 84D: | 8.0% |
| Lanol ™ 99: | 5.0% |
| Water: | q.s. for 100% |
| Pigments and inorganic fillers: | 10.0% |
| Self-invertible inverse latex (3): | 1.2% |
| Preservative: | 0.2% |
| Fragrance: | 0.4% |

EXAMPLE 25

Antisun Milk

| FORMULA | |
|---|---|
| Sepiperl ™ N: | 3.5% |
| Lanol ™ 37T: | 10.0% |
| Parsol ™ NOX: | 5.0% |
| Eusolex ™ 4360: | 2.0% |
| Water: | q.s. for 100% |
| Self-invertible inverse latex (4): | 1.8% |
| Preservative: | 0.2% |
| Fragrance: | 0.4% |

EXAMPLE 26

Gel for the Outline of the Eyes

| FORMULA | |
|---|---|
| Self-invertible inverse latex (1): | 2.0% |
| Fragrance: | 0.06% |
| Sodium pyrrolidinonecarboxylate: | 0.2% |
| Dow Corning ™ 245 Fluid: | 2.0% |
| Water: | q.s. for 100% |

EXAMPLE 27

Leave-on Care Composition

| FORMULA | |
|---|---|
| Self-invertible inverse latex (2): | 1.5% |
| Fragrance: | q.s. |
| Preservative: | q.s. |
| Dow Corning ™ X2 8360: | 5.0% |
| Dow Corning ™ Q2 1401: | 15.0% |
| Water: | q.s. for 100% |

EXAMPLE 28

Slimming Gel

| FORMULA | |
|---|---|
| Self-invertible inverse latex (4): | 5% |
| Ethanol: | 30% |
| Menthol: | 0.1% |
| Caffeine: | 2.5% |
| *Ruscus* extract: | 2% |
| *Ivy* extract: | 2% |
| Sepicide ™ HB: | 1% |
| Water: | q.s. for 100% |

EXAMPLE 29

Alcohol-Free Soothing Aftershave Balm

| | FORMULA | |
|---|---|---|
| A | Lipacide ™ PVB: | 1.0% |
| | Lanol ™ 99: | 2.0% |
| | Sweet almond oil: | 0.5% |
| B | Self-invertible inverse latex (3): | 3.5% |
| C | Water: | q.s. for 100% |
| D | Fragrance: | 0.4% |
| | Sepicide ™ HB: | 0.4% |
| | Sepicide ™ CI: | 0.2% |

EXAMPLE 30

Refreshing Aftershave Gel

| | FORMULA | |
|---|---|---|
| A | Lipacide ™ PVB: | 0.5% |
| | Lanol ™ 99: | 5.0% |
| | Self-invertible inverse latex (2): | 2.5% |
| B | Water: | q.s. for 100% |
| C | Micropearl ™ LM: | 0.5% |
| | Fragrance: | 0.2% |
| | Sepicide ™ HB: | 0.3% |
| | Sepicide ™ CI: | 0.2% |

EXAMPLE 31

Care Product for Greasy Skin

| | FORMULA | |
|---|---|---|
| A | Micropearl ™ M310: | 1.0% |
| | Self-invertible inverse latex (4): | 5.0% |
| | Octyl isononanoate: | 4.0% |
| B | Water: | q.s. for 100% |
| C | Sepicontrol ™ A5: | 4.0% |
| | Fragrance: | 0.1% |
| | Sepicide ™ HB: | 0.3% |
| | Sepicide ™ CI: | 0.2% |
| D | Capigel ™ 98: | 0.5% |
| | Water: | 10% |

EXAMPLE 32

Cream comprising AHAs

| | FORMULA | |
|---|---|---|
| A | Montanov ™ 68: | 5.0% |
| | Lipacide ™ PVB: | 1.05% |
| | Lanol ™ 99: | 10.0% |
| B | Water: | q.s. for 100% |
| | Gluconic acid: | 1.5% |
| | Triethanolamine: | 0.9% |
| C | Self-invertible inverse latex (1): | 1.5% |
| D | Fragrance: | 0.4% |
| | Sepicide ™ HB: | 0.2% |
| | Sepicide ™ CI: | 0.4% |

EXAMPLE 33

Nonfatty Self-Tanning Product for the Face and Body

| | FORMULA | |
|---|---|---|
| A | Lanol ™ 2681: | 3.0% |
| | Self-invertible inverse latex (4): | 2.5% |
| B | Water: | q.s. for 100% |
| | Dihydroxyacetone: | 3.0% |
| C | Fragrance: | 0.2% |
| | Sepicide ™ HB: | 0.8% |
| | Sodium hydroxide: | q.s. pH = 5 |

EXAMPLE 34

Antisun Milk Comprising Tahitian Monoi Oil

| | FORMULA | |
|---|---|---|
| A | Tahitian monoi oil: | 10% |
| | Lipacide ™ PVB: | 0.5% |
| | Self-invertible inverse latex (2): | 2.2% |
| B | Water: | q.s. for 100% |
| C | Fragrance: | 0.1% |
| | Sepicide ™ HB: | 0.3% |
| | Sepicide ™ CI: | 0.1% |
| | Octyl methoxycinnamate: | 4.0% |

EXAMPLE 35

Antisun Care Product for the Face

| | FORMULA | |
|---|---|---|
| A | Cyclomethicone and dimethiconol: | 4.0% |
| | Self-invertible inverse latex (3): | 3.5% |
| B | Water: | q.s. for 100% |
| C | Fragrance: | 0.1% |
| | Sepicide ™ HB: | 0.3% |
| | Sepicide ™ CI: | 0.21% |
| | Octyl methoxycinnamate: | 5.0% |
| | Titanium oxide-coated mica: | 2.0% |
| | Lactic acid: | q.s. for pH 6.5 |

EXAMPLE 36

Sun-Free Tanning Emulsion

| | FORMULA | |
|---|---|---|
| A | Lanol ™ 99: | 15% |
| | Montanov ™ 68: | 5.0% |
| | Octyl para-methoxycinnamate: | 3.0% |
| B | Water: | q.s. for 100% |
| | Dihydroxyacetone: | 5.0% |
| | Monosodium phosphate: | 0.2% |
| C | Self-invertible inverse latex (4): | 0.5% |
| D | Fragrance: | 0.3% |
| | Sepicide ™ HB: | 0.8% |
| | Sodium hydroxide: | q.s. pH 7.5 |

EXAMPLE 37

Sheen Gel

| FORMULA | |
|---|---|
| Self-invertible inverse latex (1): | 1.5% |
| Volatile silicone: | 25% |
| Monopropylene glycol: | 25% |
| Demineralized water: | 10% |
| Glycerol: | q.s. for 100% |

EXAMPLE 38

Slimming Gel

| FORMULA | |
|---|---|
| Self-invertible inverse latex (2): | 1.5% |
| Isononyl isononanoate: | 2% |
| Caffeine: | 5% |
| Ethanol: | 40% |
| Micropearl ™ LM: | 2% |
| Demineralized water: | q.s. for 100% |
| Preservative, fragrance: | q.s. |

EXAMPLE 39

Make-Up-Removing Milk

| FORMULA | |
|---|---|
| Simulsol ™ 165: | 4% |
| Montanov ™ 202: | 1% |
| Caprylate/caprate triglyceride: | 15% |
| Pecosil ™ DCT: | 1% |
| Demineralized water: | q.s. for 100% |
| Capigel ™ 98: | 0.5% |
| Self-invertible inverse latex (3): | 1% |
| Proteol ™ Oat: | 2% |
| Sodium hydroxide: | q.s. for pH = 7 |

EXAMPLE 40

Rinse-Off Restructuring Cream Mask for Stressed and Embrittled Hair

| FORMULA | |
|---|---|
| Ketrol ™ T: | 0.5% |
| Pecosil ™ SPP50: | 0.75% |
| N-Cocoyl amino acids: | 0.70% |
| Butylene glycol: | 3.0% |
| Self-invertible inverse latex (1): | 3.0% |
| Montanov ™ 82: | 3.0% |
| Jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| Fragrance: | 0.2% |
| Water: | q.s. for 100% |

EXAMPLE 41

Antisun Cream

| FORMULA | |
|---|---|
| Simulsol ™ 165: | 3% |
| Montanov ™ 202: | 2% |
| $C_{12}$-$C_{15}$ benzoate: | 8% |
| Pecosil ™ PS 100: | 2% |
| Dimethicone: | 2% |
| Cyclomethicone: | 5% |
| Octyl para-methoxycinnamate: | 6% |
| Benzophenone-3: | 4% |
| Titanium oxide: | 8% |
| Xanthan gum: | 0.2% |
| Butylene glycol: | 5% |
| Demineralized water: | q.s. for 100% |
| Self-invertible inverse latex (2): | 1.5% |
| Preservative, fragrance: | q.s. |

EXAMPLE 42

Combination Skin Care Gel

| FORMULA | |
|---|---|
| Self-invertible inverse latex (3): | 4% |
| Vegetable squalane: | 5% |
| Dimethicone: | 1.5% |
| Sepicontrol ™ A5: | 4% |
| Xanthan gum: | 0.3% |
| Water: | q.s. for 100% |
| Preservative, fragrance: | q.s. |

EXAMPLE 43

Hair Lotion

| FORMULA | |
|---|---|
| Butylene glycol: | 3.0% |
| Self-invertible inverse latex (4): | 3% |
| Simulsol ™ 1293: | 3.0% |
| Lactic acid: | q.s. pH = 6 |
| Sepicide ™ HB: | 0.2% |
| Sepicide ™ CI: | 0.3% |
| Fragrance: | 0.3% |
| Water: | q.s. for 100% |

EXAMPLE 44

Protective and Relaxing Shampoo

| FORMULA | |
|---|---|
| Amonyl ™ 675 SB: | 5.0% |
| 28% sodium lauryl ether sulfate: | 35.0% |
| Composition of example 1: | 3.0% |
| Sepicide ™ HB: | 0.5% |
| Sepicide ™ CI: | 0.3% |
| Sodium hydroxide: | q.s. pH = 7.2 |
| Fragrance: | 0.3% |
| Colorant (FDC Blue 1/Yellow 5): | q.s. |
| Water: | q.s. for 100% |

EXAMPLE 45

Leave-on Protector; Antistress Formulation Care Product for Hair

| FORMULA | |
|---|---|
| Ketrol ™ T: | 0.5% |
| Mixture of cocoyl amino acids: | 3.0% |
| Butylene glycol: | 5.0% |
| DC 1501: | 5.0% |
| Composition of example 2: | 4.0% |
| Sepicide ™ HB: | 0.5% |
| Sepicide ™ CI: | 0.3% |
| Fragrance: | 0.3% |
| Water: | q.s. for 100% |

EXAMPLE 46

Vitamin-Comprising Cream

| FORMULA | |
|---|---|
| Simulsol ™ 165: | 5% |
| Montanov ™ 202: | 1% |
| Caprylic/capric triglycerides: | 20% |
| Vitamin A palmitate: | 0.2% |
| Vitamin E acetate: | 1% |
| Micropearl ™ M 305: | 1.5% |
| Composition of example 3: | 2% |
| Water: | q.s. for 100% |
| Preservative, fragrance: | q.s. |

The definitions of the commercial products used in the examples are as follows:

Simulsol™ 1293 is hydrogenated and polyethoxylated castor oil, with an ethoxylation number equal to 40, sold by Seppic.

Capigel™ 98 is a liquid thickener based on acrylate copolymer, sold by Seppic.

Ketrol™ T is xanthan gum, sold by Kelco.

Lanol™ 99 is isononyl isononanoate, sold by Seppic.

DC1501 is a mixture of cyclopentasiloxane and dimethiconol, sold by Dow Chemical.

Montanov™ 82 is an emulsifying agent based on cetearyl alcohol and on cocoyl glucoside.

Montanov™ 68 (cetearyl glucoside) is a self-emulsifiable composition as described in WO 92/06778, sold by Seppic.

Micropearl™ M 100 is an ultrafine powder with a very soft feel and with a matifying action, sold by Matsumo.

Sepicide™ CI, imidazolidinyl urea, is a preservative, sold by Seppic.

Pemulen™ TR is an acrylic polymer, sold by Goodrich.

Simulsol™ 165 is a self-emulsifiable glyceryl stearate, sold by Seppic.

Lanol™ 1688 is an emollient ester having a non-greasy effect, sold by Seppic.

Lanol™ 14M and Lanol S are consistency factors, sold by Seppic.

Sepicide™ HB, which is a mixture of phenoxyethanol, methylparaben, ethylparaben, propylparaben and butyl-paraben, is a preservative, sold by Seppic.

Monteine™ CA is a moisturizing agent, sold by Seppic.

Schercemol™ OP is an emollient ester having a non-greasy effect.

Lanol™ P is an additive having a stabilizing effect, sold by Seppic.

Parsol™ MCX is octyl para-methoxycinnamate, sold by Givaudan.

Sepiperl™ N is a pearlescent agent, sold by Seppic, based on a mixture of alkyl polyglucosides, such as those described in WO 95/13863.

Micropearl™ SQL is a mixture of microparticles including squalane, which is released under the action of massaging; it is sold by Matsumo.

Lanol™ 99 is isononyl isononanoate, sold by Seppic.

Lanol™ 37T is glyceryl triheptanoate, sold by Seppic.

Solagum™ L is a carrageenan, sold by Seppic.

Marcol™ 82 is a liquid paraffin, sold by Exxon.

Lanol™ 84D is dioctyl malate, sold by Seppic.

Parsol NOX™ is a sunscreen, sold by Givaudan.

Eusolex™ 4360 is a sunscreen, sold by Merck.

Dow Corning™ 245 Fluid is cyclomethicone, sold by Dow Corning.

Lipacide™ PVB is an acylated wheat protein hydrolysate, sold by Seppic.

Micropearl™ is a mixture of squalane, polymethyl methacrylate and menthol, sold by Seppic.

Sepicontrol™ A5 is a mixture of capryloyl glycine, sarcosine and *Cinnamomum zeylanicum* extract, sold by Seppic, such as those described in international patent application PCT/FR98/01313, filed on 23 Jun. 1998.

Lanol™ 2681 is a coco-caprylate/caprate mixture, sold by Seppic.

Montanov™ 202 is an APG/fatty alcohols composition, such as described in WO 98/47610, sold by Seppic.

The invention claimed is:

1. A composition in the form of a self-invertible inverse latex comprising, for 100% of its weight:
   (a) from 50% by weight to 70% by weight of a crosslinked anionic polyelectrolyte (P) obtained by polymerization of:
   (i) at least one neutral monomer of formula (I):

in which the R1 radical represents a linear or branched aliphatic radical comprising from 8 to 20 carbon atoms and n represents a number greater than or equal to one and less than or equal to thirty;
   (ii) at least one neutral monomer selected from the group consisting of: acrylamide, N,N-dimethylacrylamide, N-[tris(hydroxymethyl)methyl]acrylamide and 2-hydroxyethyl acrylate; and
   (iii) at least one monomer comprising a strong acid functional group and/or at least one monomer comprising a weak acid functional group;
   (b) from 4% by weight to 10% by weight of an emulsifying system ($S_1$) of water-in-oil (W/O) type;
   (c) from 1% by weight to 10% by weight of an emulsifying system ($S_2$) of oil-in-water (O/W) type comprising a proportion greater than or equal to 50% by weight of a surfactant composition (C), said surfactant composition (C) comprising, for 100 mol %:
   1)—a proportion of from 10 mol % to 50 mol % of a composition ($C_{II}$) comprising, per 100 mol %:
      α)—from 60 mol % to 100 mol % of a compound of formula (II):

in which:
   R2 represents a linear or branched alkyl radical comprising 12 carbon atoms,
   $T_1$ represents a hydrogen atom or a (—$CH_2$—$CH_2$—O—)$_{m1}$—H radical in which m1 is an integer of zero to ten inclusive,
   $T_2$, which is identical to or different from $T_1$, represents a hydrogen atom or a (—$CH_2$—$CH_2$—O—)$_{m2}$—H radical in which m2 is an integer of zero to ten inclusive, and
   $T_3$, which is identical to or different from $T_1$ and $T_2$, represents a hydrogen atom or a (—$CH_2$—$CH_2$—O—)$_{m3}$—H radical in which m3 is an integer of zero to ten inclusive,
   it being understood that the sum m1+m2+m3 is greater than 0 and less than or equal to ten;

β optionally up to 40 mol % of a compound of formula (II'):

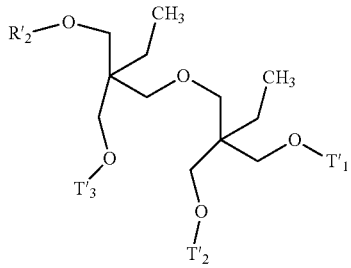

in which:
- R'$_2$ represents a linear or branched alkyl radical comprising 14 carbon atoms,
- T'$_1$ represents a hydrogen atom or a (—CH$_2$—CH$_2$—O—)$_{m1}$—H radical in which m1 is an integer of zero to ten inclusive,
- T'$_2$, which is identical to or different from T'$_1$, represents a hydrogen atom or a (—CH$_2$—CH$_2$—O—)$_{m2}$—H radical in which m2 is an integer of zero to ten inclusive, and
- T'$_3$, which is identical to or different from T'$_1$ and T'$_2$, represents a hydrogen atom or a (—CH$_2$—CH$_2$—O—)$_{m3}$—H radical in which m3 is an integer of zero to ten inclusive,
- it being understood that the sum m1+m2+m3 is greater than 0 and less than or equal to ten; and γ)—optionally up to 10 mol % of a compound of formula (II"):

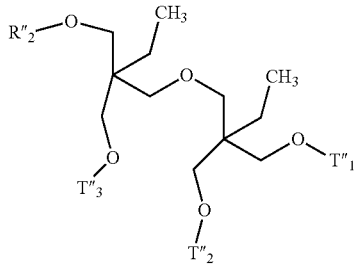

in which:
- R"$_2$ represents a linear or branched alkyl radical comprising 16 carbon atoms,
- T"$_1$ represents a hydrogen atom or a (—CH$_2$—CH$_2$—O—)$_{m1}$—H radical in which m1 is an integer of zero to ten inclusive,
- T"$_2$, which is identical to or different from T"$_1$, represents a hydrogen atom or a (—CH$_2$—CH$_2$—O—)$_{m2}$—H radical in which m2 is an integer of zero to ten inclusive, and
- T"$_3$, which is identical to or different from T"$_1$ and T"$_2$, represents a hydrogen atom or a (—CH$_2$—CH$_2$—O—)$_{m3}$—H radical in which m3 is an integer of zero to ten inclusive,
- it being understood that the sum m1+m2+m3 is greater than 0 and less than or equal to ten;

2)—a proportion of from 50 mol % to 90 mol % of a composition (C$_{III}$) comprising, per 100 mol %:
α)—from 60 mol % to 100 mol % of a compound of formula (III):

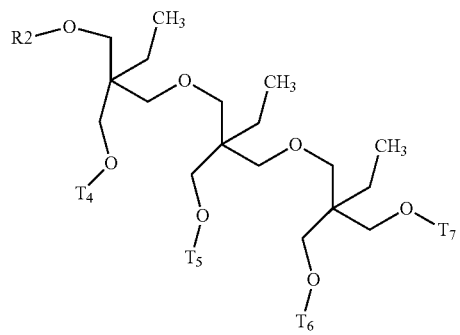

or of its isomer of formula (IV):

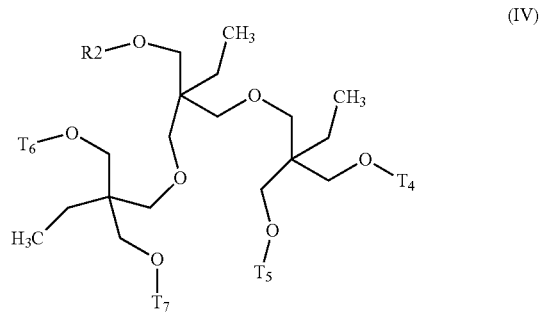

or of a mixture thereof,
in which formulae (III) and (IV):
- R2 represents a linear or branched alkyl radical comprising 12 carbon atoms,
- T$_4$ represents a hydrogen atom or a (—CH$_2$—CH$_2$—O—)$_{m4}$—H radical in which m4 is an integer of zero to ten inclusive,
- T$_5$, which is identical to or different from T$_4$, represents a hydrogen atom or a (—CH$_2$—CH$_2$—O—)$_{m5}$—H radical in which m5 is an integer of zero to ten inclusive,
- T$_6$, which is identical to or different from T$_4$ and T$_5$, represents a hydrogen atom or a (—CH$_2$—CH$_2$—O—)$_{m6}$—H radical in which m6 is an integer of zero to ten inclusive,
- T$_7$, which is identical to or different from T$_4$, T$_5$ and T$_6$, represents a hydrogen atom or a (—CH$_2$—CH$_2$—O—)$_{m7}$—H radical in which m7 is an integer of zero to ten inclusive, it being understood that the sum m4+m5+m6+m7 is greater than 0 and less than or equal to ten;

β)—optionally up to 40 mol % of a compound of formula (III'):

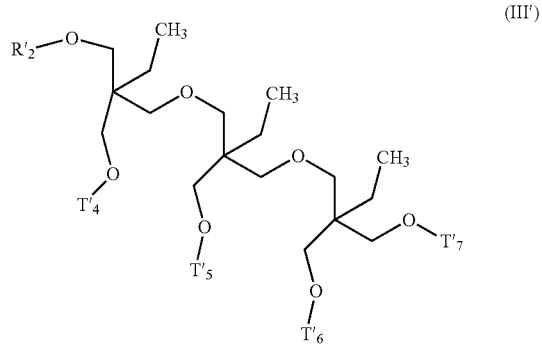

or of its isomer of formula (IV'):

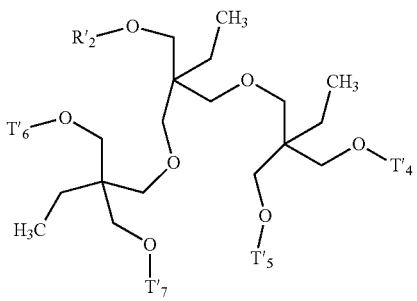

(IV')

or of a mixture thereof, in which formulae (III') and (IV'):
R'$_2$ represents a linear or branched alkyl radical comprising 14 carbon atoms,
T'$_4$ represents a hydrogen atom or a (—CH$_2$—CH$_2$—O—)$_{m4}$—H radical in which m4 is an integer of zero to ten inclusive,
T'$_5$, which is identical to or different from T'$_4$, represents a hydrogen atom or a (—CH$_2$—CH$_2$—O—)$_{m5}$—H radical in which m5 is an integer of zero to ten inclusive,
T'$_6$, which is identical to or different from T'$_4$ and T'$_5$, represents a hydrogen atom or a (—CH$_2$—CH$_2$—O—)$_{m6}$—H radical in which m6 is an integer of zero to ten inclusive, and
T'$_7$, which is identical to or different from T'$_4$, T'$_5$ and T'$_6$, represents a hydrogen atom or a (—CH$_2$—CH$_2$—O—)$_{m7}$—H radical in which m7 is an integer of zero to ten inclusive,
it being understood that the sum m4+m5+m6+m7 is greater than 0 and less than or equal to ten; and
γ)—optionally up to 10 mol % of a compound of formula (III"):

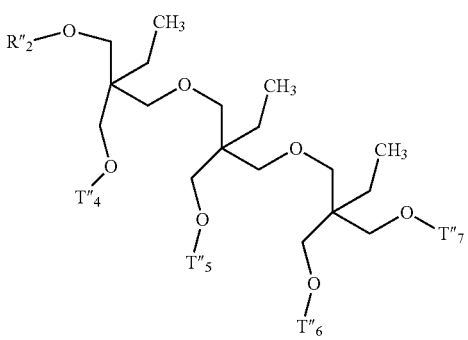

(III")

or of its isomer of formula (IV"):

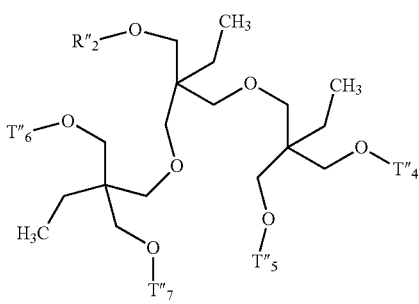

(IV")

or of a mixture thereof, in which formulae (III") and (IV"):
R"$_2$ represents a linear or branched alkyl radical comprising 16 carbon atoms,
T"4 represents a hydrogen atom or a (—CH$_2$—CH$_2$—O—)$_{m4}$—H radical in which m4 is an integer of zero to ten inclusive,
T"$_5$, which is identical to or different from T"$_4$, represents a hydrogen atom or a (—CH$_2$—CH$_2$—O—)$_{m5}$—H radical in which m5 is an integer of zero to ten inclusive,
T"$_6$, which is identical to or different from T"$_4$ and T"$_5$, represents a hydrogen atom or a (—CH$_2$—CH$_2$—O—)$_{m6}$—H radical in which m6 is an integer of zero to ten inclusive, and
T"$_7$, which is identical to or different from T"$_4$, T"$_5$ and T"$_6$, represents a hydrogen atom or a (—CH$_2$—CH$_2$—O—)$_{m7}$—H radical in which m7 is an integer of zero to ten inclusive,
it being understood that the sum m4+m5+m6+m7 is greater than 0 and less than or equal to ten;
(d) from 15% by weight to 45% by weight of at least one oil, and
(e) from 0% by weight to 5% by weight of water.

2. The composition as defined in claim 1, for which, in the formula (I), the R1 radical represents a lauryl radical or a stearyl radical.

3. The composition as defined in claim 1, for which, in the formula (I), n is greater than or equal to two and less than or equal to twenty.

4. The composition as defined in claim 1, for which, in the polyelectrolyte (P), the monomer units comprising a strong acid functional group result from 2-methyl-2-[(1-oxo-2-propenyl)amino]-1-propanesulfonic acid partially or completely salified as sodium salt, as potassium salt or as ammonium salt and the monomer units comprising a weak acid functional group result from acrylic acid or from methacrylic acid partially salified as sodium salt, as potassium salt or as ammonium salt.

5. The composition as defined in claim 1, for which the polyelectrolyte P comprises, as molar percentage, from 0.5% to 10% of a monomer unit resulting from the monomer of formula (I) as defined above.

6. The composition as defined in claim 1, for which said surfactant composition (C) additionally comprises:
3)—up to 5 mol % of a composition (C$_V$) comprising, per 100 mol %:
α)—from 60 mol % to 100 mol % of a compound of formula (V):

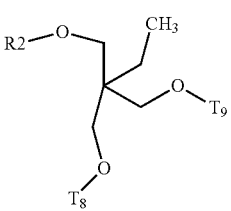

(V)

in which:
R2 represents a linear or branched alkyl radical comprising 12 carbon atoms,
T$_8$ represents a hydrogen atom or a (—CH$_2$—CH$_2$—O—)$_{m8}$—H radical in which m8 is an integer of zero to ten inclusive, T$_9$, which is identical to or different from T$_8$, represents a hydrogen atom or a (—CH$_2$—CH$_2$—O—)$_{m9}$—H radical in which m9 is an integer of zero to ten inclusive, and it being understood that the sum m8+m9 is greater than 0 and less than or equal to ten;

β)—optionally up to 40 mol % of a compound of formula (V'):

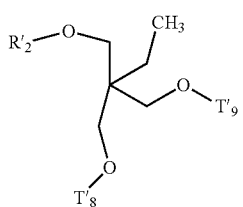

in which:
R'$_2$ represents a linear or branched alkyl radical comprising 14 carbon atoms,
T'$_8$ represents a hydrogen atom or a (—CH$_2$—CH$_2$—O—)$_{m8}$—H radical in which m8 is an integer of zero to ten inclusive,
T'$_9$, which is identical to or different from T'$_8$, represents a hydrogen atom or a (—CH$_2$—CH$_2$—O—)$_{m9}$—H radical in which m9 is an integer of zero to ten inclusive, and
it being understood that the sum m8+m9 is greater than 0 and less than or equal to ten; and
γ)—optionally up to 10 mol % of a compound of formula (V"):

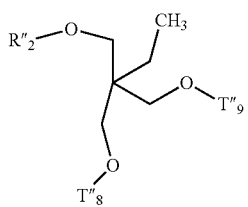

in which:
R"$_2$ represents a linear or branched alkyl radical comprising 16 carbon atoms,
T"8 represents a hydrogen atom or a (—CH$_2$—CH$_2$—O—)$_{m8}$—H radical in which m8 is an integer of zero to ten inclusive,
T"$_9$, which is identical to or different from T"$_8$, represents a hydrogen atom or a (—CH$_2$—CH$_2$—O—)$_m$9—H radical in which m9 is an integer of zero to ten inclusive, and
it being understood that the sum m8+m9 is greater than 0 and less than or equal to ten.

7. The composition as defined in claim 1, for which said surfactant composition (C) additionally comprises:
4)—up to 5 mol % of a composition (C$_{VI}$) comprising, per 100 mol %:
α)—from 60 mol % to 100 mol % of a compound of formula (VI):

R2-(—CH$_2$—CH$_2$—O—)$_{m10}$—H (VI)

in which R2 represents a linear or branched alkyl radical comprising 12 carbon atoms and m10 is an integer of zero to ten inclusive;

β)—optionally up to 40 mol % of a compound of formula (VI'):

R'$_2$—(—CH$_2$—CH$_2$—O—)$_{m10}$—H (VI')

in which R'$_2$ represents a linear or branched alkyl radical comprising 14 carbon atoms and m10 is an integer of zero to ten inclusive; and γ)—optionally up to 10 mol % of a compound of formula (VI"):

R"$_2$—(—CH$_2$—CH$_2$—O—)$_{m10}$—H (VI")

in which R"$_2$ represents a linear or branched alkyl radical comprising 16 carbon atoms and m10 is an integer of zero to ten inclusive.

8. The composition as defined in claim 1, for which said surfactant composition (C) comprises:
1)—a proportion of from 20 mol % to 50 mol % of a composition (C$_{II}$) as defined above;
2)—a proportion of from 20 mol % to 80 mol % of a composition (C$_{III}$) as defined above.

9. The composition as defined in claim 1, for which, in said surfactant composition (C):
1)—said composition (C$_{II}$) comprises, per 100 mol %:
α)—from 60 mol % to 80 mol % of the compound of formula (II),
β)—from 15 mol % to 30 mol % of the compound of formula (II'), and
γ)—up to 10 mol % of the compound of formula (II"), and
2)—said composition (C$_{III}$) comprises, per 100 mol %:
α)—from 60 mol % to 80 mol % of the compound of formula (III), of its isomer of formula (IV) or of the mixture of these isomers,
β)—from 15 mol % to 30 mol % of the compound of formula (III'), of its isomer of formula (IV') or of the mixture of these isomers, and
γ)—up to 10 mol % of the compound of formula (III"), of its isomer of formula (IV") or of the mixture of these isomers.

10. The composition as defined in claim 1, in which said emulsifying system (S$_2$) of oil-in-water (O/W) type consists of 100% by weight of said surfactant composition (C).

11. The composition as defined in claim 1, in which said emulsifying system (S$_2$) of oil-in-water (O/W) type comprises, per 100% of its weight:
from 10% by weight to 40% by weight of hepta-ethoxylated lauryl alcohol; and
from 60% by weight to 90% by weight of said surfactant composition (C).

12. The composition as defined in claim 1, for which, in the polyelectrolyte (P), the monomer unit resulting from the monomer of formula (I) is a monomer unit resulting from tetraethoxylated lauryl acrylate.

13. The composition as defined in claim 12, in which the polyelectrolyte (P) is selected from the group consisting of:
crosslinked copolymers of acrylic acid partially salified in the sodium salt or ammonium salt form, of acrylamide and of tetraethoxylated lauryl acrylate;
crosslinked copolymers of 2-methyl-2-[(1-oxo-2-propenyl)amino]-1-propanesulfonic acid partially salified in the sodium salt or ammonium salt form, of acrylamide and of tetraethoxylated lauryl acrylate;
crosslinked copolymers of 2-methyl-2-[(1-oxo-2-propenyl)amino]-1-propanesulfonic acid partially salified in the sodium salt or ammonium salt form, of 2-hydroxyethyl acrylate and of tetraethoxylated lauryl acrylate;

crosslinked copolymers of acrylamide, of 2-methyl-2-[(1-oxo-2-propenyl)amino]-1-propanesulfonic acid, of acrylic acid partially salified in the sodium salt or ammonium salt form and of tetraethoxylated lauryl acrylate;

copolymers of 2-methyl-2-[(1-oxo-2-propenyl)amino]-1-propanesulfonic acid partially salified in the sodium salt or ammonium salt form, of acrylamide, of vinylpyrrolidone and of tetraethoxylated lauryl acrylate; and crosslinked copolymers of 2-methyl-2-[(1-oxo-2-propenyl)amino]-1-propanesulfonic acid partially or completely salified in the sodium salt form, of acrylic acid partially salified in the sodium salt or ammonium salt form, of 2-hydroxyethyl acrylate, of tris(hydroxy-methyl)aminomethylacrylamide and of tetraethoxylated lauryl acrylate.

14. The composition as defined in claim 1, in which the crosslinked anionic polyelectrolyte (P) comprises, per 100% of monomers employed:

from 40 mol % to 80 mol % of monomer units resulting from a monomer comprising a strong acid functional group;

from 15 mol % to 55 mol % of monomer units resulting from a neutral monomer other than the compound of formula (I) as defined above; and from 1 mol % to 5 mol % of monomer units resulting from a monomer of formula (I) as defined above.

15. A method of preparing a cosmetic, dermopharmaceutical or pharmaceutical topical composition, comprising adding the composition in the form of a self-invertible inverse latex as defined in claim 1 to said cosmetic, dermopharmaceutical or pharmaceutical topical composition.

16. A cosmetic, dermopharmaceutical or pharmaceutical topical composition, comprising as thickening and/or emulsifying agent, an effective amount of the composition as defined in claim 1.

* * * * *